United States Patent
Kaula et al.

(10) Patent No.: US 8,868,199 B2
(45) Date of Patent: Oct. 21, 2014

(54) SYSTEM AND METHOD OF COMPRESSING MEDICAL MAPS FOR PULSE GENERATOR OR DATABASE STORAGE

(71) Applicant: Greatbatch Ltd., Clarence, NY (US)

(72) Inventors: Norbert Kaula, Arvada, CO (US);
Yohannes Iyassu, Denver, CO (US);
Carl Mosley, Ormond Beach, FL (US);
Scott Drees, Dallas, TX (US)

(73) Assignee: Greatbatch Ltd., Clarence, NY (US)

(*) Notice: Subject to any disclaimer, the term of this patent is extended or adjusted under 35 U.S.C. 154(b) by 0 days.

(21) Appl. No.: 13/973,363

(22) Filed: Aug. 22, 2013

(65) Prior Publication Data
US 2014/0067017 A1    Mar. 6, 2014

Related U.S. Application Data

(63) Continuation-in-part of application No. 13/604,197, filed on Sep. 5, 2012.

(60) Provisional application No. 61/695,433, filed on Aug. 31, 2012, provisional application No. 61/695,407, filed on Aug. 31, 2012, provisional application No. 61/695,721, filed on Aug. 31, 2012, provisional application No. 61/695,676, filed on Aug. 31, 2012, provisional application No. 61/824,296, filed on May 16, 2013.

(51) Int. Cl.
| | |
|---|---|
| *A61N 1/00* | (2006.01) |
| *A61N 1/372* | (2006.01) |
| *G06F 19/00* | (2011.01) |
| *G06T 19/20* | (2011.01) |
| *A61N 1/36* | (2006.01) |

(52) U.S. Cl.
CPC ..... *A61N 1/37252* (2013.01); *G06T 2219/2012* (2013.01); *G06F 19/322* (2013.01); *A61N 1/37247* (2013.01); *G06T 2219/2021* (2013.01); *A61N 1/36128* (2013.01); *G06T 2210/41* (2013.01); *G06T 19/20* (2013.01)
USPC .......................................................... 607/59

(58) Field of Classification Search
USPC .......................................................... 607/59
See application file for complete search history.

(56) References Cited

U.S. PATENT DOCUMENTS

| | | | |
|---|---|---|---|
| 4,432,360 A | 2/1984 | Mumford et al. | |
| 5,286,202 A | 2/1994 | De Gyarfas et al. | |

(Continued)

FOREIGN PATENT DOCUMENTS

| | | |
|---|---|---|
| EP | 0761255 | 3/1997 |
| EP | 1192972 | 4/2002 |

(Continued)

OTHER PUBLICATIONS

Extended European Search Report issued for Patent Application No. 13182618.2, dated Dec. 13, 2013, 7 pgs.

(Continued)

*Primary Examiner* — Robert N Wieland
(74) *Attorney, Agent, or Firm* — Haynes and Boone, LLP

(57) ABSTRACT

The present disclosure involves a method of data-reducing and storing a sensation map. A sensation map associated with a patient is provided. The sensation map includes a graphical depiction of a sensation experienced by the patient. The sensation may be pain or paresthesia experienced by the patient in response to an electrical stimulation therapy. A data file is generated. The data file has a data size less than a data size of the sensation map. The data file contains digital information allowing a reconstruction of the sensation map. Electronic communication is then established with an implanted medical device located inside the patient's body. Thereafter, the data file is sent to the implanted medical device for storage. The stored data files are retrievable by another clinician programmer later to reconstruct the sensation map.

33 Claims, 19 Drawing Sheets

(56) References Cited

U.S. PATENT DOCUMENTS

| | | |
|---|---|---|
| 5,304,206 A | 4/1994 | Baker, Jr. et al. |
| 5,312,446 A | 5/1994 | Holschbach et al. |
| 5,370,672 A | 12/1994 | Fowler et al. |
| 5,383,914 A | 1/1995 | O'Phelan |
| 5,421,830 A | 6/1995 | Epstein et al. |
| 5,628,776 A | 5/1997 | Paul et al. |
| 5,713,937 A | 2/1998 | Nappholz et al. |
| 5,722,999 A | 3/1998 | Snell |
| 5,724,996 A | 3/1998 | Piunti |
| 5,819,740 A | 10/1998 | Muhlenberg |
| 5,842,976 A | 12/1998 | Williamson |
| 5,879,374 A | 3/1999 | Powers et al. |
| 5,905,500 A | 5/1999 | Kamen et al. |
| 5,938,690 A | 8/1999 | Law et al. |
| 5,973,968 A | 10/1999 | Schu et al. |
| 6,016,447 A | 1/2000 | Juran et al. |
| 6,016,448 A | 1/2000 | Busacker et al. |
| 6,052,624 A | 4/2000 | Mann |
| 6,083,156 A | 7/2000 | Lisiecki |
| 6,148,233 A | 11/2000 | Owen et al. |
| 6,154,675 A | 11/2000 | Juran et al. |
| 6,216,036 B1 | 4/2001 | Jenkins et al. |
| 6,246,414 B1 | 6/2001 | Kawasaki |
| 6,249,705 B1 | 6/2001 | Snell |
| 6,278,890 B1 | 8/2001 | Chassaing et al. |
| 6,307,554 B1 | 10/2001 | Arai et al. |
| 6,308,102 B1 | 10/2001 | Sieracki et al. |
| 6,345,200 B1 | 2/2002 | Mouchawar et al. |
| 6,386,882 B1 | 5/2002 | Linberg |
| 6,442,432 B2 | 8/2002 | Lee |
| 6,525,727 B1 | 2/2003 | Junkins et al. |
| 6,564,104 B2 | 5/2003 | Nelson et al. |
| 6,587,104 B1 | 7/2003 | Hoppe |
| 6,611,267 B2 | 8/2003 | Migdal et al. |
| 6,622,048 B1 | 9/2003 | Mann et al. |
| 6,669,631 B2 | 12/2003 | Norris et al. |
| 6,786,405 B2 | 9/2004 | Wiedenhoefer |
| 6,852,080 B2 | 2/2005 | Bardy |
| 6,882,982 B2 | 4/2005 | McMenimen et al. |
| 6,895,280 B2 | 5/2005 | Meadows et al. |
| 6,920,360 B2 | 7/2005 | Lee et al. |
| 6,931,155 B1 | 8/2005 | Gioia |
| 6,961,448 B2 | 11/2005 | Nichols et al. |
| 6,961,617 B1 | 11/2005 | Snell |
| 7,003,349 B1 | 2/2006 | Andersson et al. |
| 7,034,823 B2 | 4/2006 | Dunnett |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,910 B2 | 6/2006 | Bauhahn et al. |
| 7,076,303 B2 | 7/2006 | Linberg |
| 7,087,015 B1 | 8/2006 | Comrie et al. |
| 7,092,761 B1 | 8/2006 | Cappa et al. |
| 7,107,102 B2 | 9/2006 | Daignault et al. |
| 7,142,923 B2 | 11/2006 | North et al. |
| 7,181,286 B2 | 2/2007 | Sieracki et al. |
| 7,181,505 B2 | 2/2007 | Haller et al. |
| 7,184,837 B2 | 2/2007 | Goetz |
| 7,239,926 B2 | 7/2007 | Goetz |
| 7,240,833 B2 | 7/2007 | Zarembo |
| 7,266,412 B2 | 9/2007 | Stypulkowski |
| 7,299,085 B2 | 11/2007 | Bergelson et al. |
| 7,359,751 B1 | 4/2008 | Erickson et al. |
| 7,373,204 B2 | 5/2008 | Gelfand et al. |
| 7,440,806 B1 | 10/2008 | Whitehurst et al. |
| 7,452,336 B2 | 11/2008 | Thompson |
| 7,463,927 B1 | 12/2008 | Chaouat |
| 7,474,223 B2 | 1/2009 | Nycz et al. |
| 7,481,759 B2 | 1/2009 | Whitehurst et al. |
| 7,489,970 B2 | 2/2009 | Lee et al. |
| 7,496,403 B2 | 2/2009 | Cao et al. |
| 7,499,048 B2 | 3/2009 | Sieracki et al. |
| 7,505,815 B2 | 3/2009 | Lee et al. |
| 7,551,960 B2 | 6/2009 | Forsberg et al. |
| 7,602,384 B2 | 10/2009 | Rosenberg et al. |
| 7,617,002 B2 | 11/2009 | Goetz |
| 7,627,372 B2 | 12/2009 | Vaisnys et al. |
| 7,640,059 B2 | 12/2009 | Forsberg et al. |
| 7,650,888 B2 | 1/2010 | Maschke |
| 7,657,317 B2 | 2/2010 | Thacker et al. |
| 7,685,005 B2 | 3/2010 | Riff et al. |
| 7,711,603 B2 | 5/2010 | Vanker et al. |
| 7,720,549 B2 | 5/2010 | Schroeppel et al. |
| 7,747,330 B2 | 6/2010 | Nolan et al. |
| 7,774,067 B2 | 8/2010 | Keacher et al. |
| 7,778,710 B2 | 8/2010 | Propato |
| 7,801,596 B2 | 9/2010 | Fischell et al. |
| 7,801,611 B2 | 9/2010 | Persen et al. |
| 7,805,199 B2 | 9/2010 | KenKnight et al. |
| 7,822,483 B2 | 10/2010 | Stone et al. |
| 7,853,323 B2 | 12/2010 | Goetz |
| 7,885,712 B2 | 2/2011 | Goetz et al. |
| 7,890,180 B2 | 2/2011 | Quiles et al. |
| 7,928,995 B2 | 4/2011 | Daignault |
| 7,934,508 B2 | 5/2011 | Behm |
| 7,940,933 B2 | 5/2011 | Corndorf |
| 7,953,492 B2 | 5/2011 | Corndorf |
| 7,953,612 B1 | 5/2011 | Palmese et al. |
| 7,957,808 B2 | 6/2011 | Dawant et al. |
| 7,978,062 B2 | 7/2011 | LaLonde et al. |
| 7,991,482 B2 | 8/2011 | Bradley |
| 8,014,863 B2 | 9/2011 | Zhang et al. |
| 8,021,298 B2 | 9/2011 | Baird et al. |
| 8,027,726 B2 | 9/2011 | Ternes |
| 8,046,241 B1 | 10/2011 | Dodson |
| 8,060,216 B2 | 11/2011 | Greenberg et al. |
| 8,068,915 B2 | 11/2011 | Lee et al. |
| 8,068,918 B2 | 11/2011 | Vallapureddy et al. |
| 8,078,440 B2 | 12/2011 | Otto et al. |
| 8,082,162 B2 | 12/2011 | Flood |
| 8,121,702 B2 | 2/2012 | King |
| 8,135,566 B2 | 3/2012 | Marshall et al. |
| 8,140,160 B2 | 3/2012 | Pless et al. |
| 8,140,167 B2 | 3/2012 | Donders et al. |
| 8,160,328 B2 | 4/2012 | Goetz et al. |
| 8,160,704 B2 | 4/2012 | Freeberg |
| 8,165,385 B2 | 4/2012 | Reeves et al. |
| 8,187,015 B2 | 5/2012 | Boyd et al. |
| 8,200,324 B2 | 6/2012 | Shen et al. |
| 8,200,340 B2 | 6/2012 | Skelton et al. |
| 8,219,206 B2 | 7/2012 | Skelton et al. |
| 8,233,991 B2 | 7/2012 | Woods et al. |
| 8,246,680 B2 | 8/2012 | Betz et al. |
| 8,249,713 B2 | 8/2012 | Fang et al. |
| 8,255,060 B2 | 8/2012 | Goetz et al. |
| 8,323,218 B2 | 12/2012 | Davis et al. |
| 8,326,433 B2 | 12/2012 | Blum et al. |
| 8,340,775 B1 | 12/2012 | Cullen et al. |
| 8,382,666 B1 | 2/2013 | Mao et al. |
| 8,386,032 B2 | 2/2013 | Bachinski et al. |
| 8,401,666 B2 | 3/2013 | Skelton et al. |
| 8,428,727 B2 | 4/2013 | Bolea et al. |
| 2001/0037220 A1 | 11/2001 | Merry et al. |
| 2003/0009203 A1 | 1/2003 | Lebel et al. |
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1* | 8/2005 | Razdan et al. ................ 345/419 |
| 2005/0277872 A1 | 12/2005 | Colby et al. |
| 2006/0020304 A1 | 1/2006 | Torgerson et al. |
| 2006/0089888 A1 | 4/2006 | Roger |
| 2006/0100832 A1 | 5/2006 | Bowman |
| 2006/0100907 A1 | 5/2006 | Holland et al. |
| 2006/0212096 A1 | 9/2006 | Stevenson |
| 2006/0241720 A1 | 10/2006 | Woods et al. |
| 2006/0242159 A1 | 10/2006 | Bishop et al. |
| 2006/0282168 A1 | 12/2006 | Sherman et al. |

(56) References Cited

U.S. PATENT DOCUMENTS

| | | |
|---|---|---|
| 2007/0078497 A1 | 4/2007 | Vandanacker |
| 2007/0093998 A1 | 4/2007 | El-Baroudi |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2007/0260292 A1 | 11/2007 | Faltys et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0058900 A1 | 3/2008 | Berthelsdorf et al. |
| 2008/0140160 A1 | 6/2008 | Goetz et al. |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0062887 A1 | 3/2009 | Mass et al. |
| 2009/0089034 A1 | 4/2009 | Penney et al. |
| 2009/0099624 A1 | 4/2009 | Kokones et al. |
| 2009/0132009 A1 | 5/2009 | Torgenson |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennett et al. |
| 2011/0093030 A1 | 4/2011 | Goetz et al. |
| 2011/0093047 A1 | 4/2011 | Davis et al. |
| 2011/0093051 A1* | 4/2011 | Davis et al. ............... 607/116 |
| 2011/0112601 A1 | 5/2011 | Meadows et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0196449 A1 | 8/2011 | Jenison |
| 2011/0196455 A1* | 8/2011 | Sieracki et al. ............... 607/62 |
| 2011/0224523 A1 | 9/2011 | Budiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0109258 A1 | 5/2012 | Cinbis et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Connor et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| EP | 2277586 | 1/2011 |
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Synalink Features, SynaMed Web Page, http://synamed.com/synalinkFeatures.html., Copyright 2010, 2 pgs.

Boston Scientific Corporation, "Boston Scientific Precision Spectra System Programming Manual", Copyright 2010, 580 pgs.

* cited by examiner

SYSTEM AND METHOD OF COMPRESSING MEDICAL MAPS FOR PULSE GENERATOR OR DATABASE STORAGE

PRIORITY DATA

The present application is a utility application of provisional U.S. Patent Application No. 61/695,433, filed on Aug. 31, 2012, entitled "System and Method of Compressing Medical Maps For Pulse Generator Or Database Storage," and a utility application of provisional U.S. Patent Application No. 61/695,407, filed on Aug. 31, 2012, entitled "Method and System of Producing 2D Representations of 3D Pain and Stimulation Maps and Implant Models on a Clinician Programmer," and a utility application of provisional U.S. Patent Application No. 61/695,721, filed on Aug. 31, 2012, entitled "Method and System of Creating, Displaying, and Comparing Pain and Stimulation Maps," and a utility application of provisional U.S. Patent Application No. 61/695,676, filed on Aug. 31, 2012, entitled "Method and System of Adjusting 3D Models of Patients on a Clinician Programmer," and a utility application of provisional U.S. Patent Application No. 61/824,296, filed on May 16, 2013, entitled "Features and Functionalities of an Advanced Clinician Programmer," and a continuation-in-part of U.S. patent application Ser. No. 13/604,197, filed on Sep. 5, 2012, entitled "Method and System for Associating Patient Records with Pulse Generators," the disclosures of each of which are hereby incorporated by reference in their entirety.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients or restore bodily functions.

Implanted medical devices (for example a neurostimulator) can be controlled using an electronic programming device such as a clinician programmer or a patient programmer. These programmers can be used by medical personnel or the patient to define the particular electrical stimulation therapy to be delivered to a target area of the patient's body, alter one or more parameters of the electrical stimulation therapy, or otherwise conduct communications with a patient. In some cases, these electronic programmers allow the creation and display of pain maps and stimulation maps as part of the pain diagnosis and communication with the patient. However, these pain/stimulation maps may be relatively large in size (i.e., contains a large amount of data). As a result, they are not suitable for storage on electronic devices with limited storage capacity. The lack of storage flexibility for existing pain/stimulation maps limits the effectiveness of using these maps and may also drive up diagnostic costs.

Therefore, although existing neurostimulation devices and methods have been generally adequate for their intended purposes, they have not been entirely satisfactory in every aspect.

SUMMARY

One aspect of the present disclosure involves an electronic apparatus for data-reducing and transmitting a sensation map of a patient. The electronic device includes: a memory storage component configured to store programming code; and a computer processor configured to execute the programming code to perform the following tasks: providing a sensation map associated with the patient, the sensation map including a graphical depiction of a sensation experienced by the patient; generating a data file having a data size less than a data size of the sensation map, wherein the data file contains digital information allowing a reconstruction of the sensation map; establishing electronic communication with an implanted medical device located inside the patient's body; and thereafter sending the data file to the implanted medical device for storage.

Another aspect of the present disclosure involves a medical system. The medical system includes: a neurostimulator configured to deliver electrical stimulation to a patient via one or more of a plurality of contacts located on a lead; and a portable electronic programmer having an electronic processor and a touch-sensitive graphical user interface, wherein the electronic programmer is configured to: provide a sensation map associated with a patient, the sensation map including a graphical depiction of a sensation experienced by the patient; generate a data file having a data size less than a data size of the sensation map, wherein the data file contains digital information allowing a reconstruction of the sensation map; establish electronic communication with the neurostimulator; and thereafter send the data file to the neurostimulator for storage.

Yet another aspect of the present disclosure involves a method of setting stimulation parameters for neurostimulation. The method comprises: providing a sensation map associated with a patient, the sensation map including a graphical depiction of a sensation experienced by the patient; generating a data file having a data size less than a data size of the sensation map, wherein the data file contains digital information allowing a reconstruction of the sensation map; establishing electronic communication with an implanted medical device located inside the patient's body; and thereafter sending the data file to the implanted medical device for storage.

One more aspect of the present disclosure involves a programmable pulse generator for delivering a stimulation therapy to a patient. The programmable pulse generator includes: a transceiver configured to electronic data via electronic communication conducted with an external clinician programmer; a memory storage configured to store the electronic data, wherein the electronic data includes: a stimulation program containing programming instructions for operating the programmable pulse generator; and a data file having a smaller data size than the sensation map and containing digital information allowing reconstruction of the sensation map that graphically depicts, on the external clinician programmer, a sensation experienced by the patient stimulation program and the data file; and a microcontroller and stimulation circuitry configured to generate electrical pulses of the stimulation therapy based on the stimulation program.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

Figure 1:
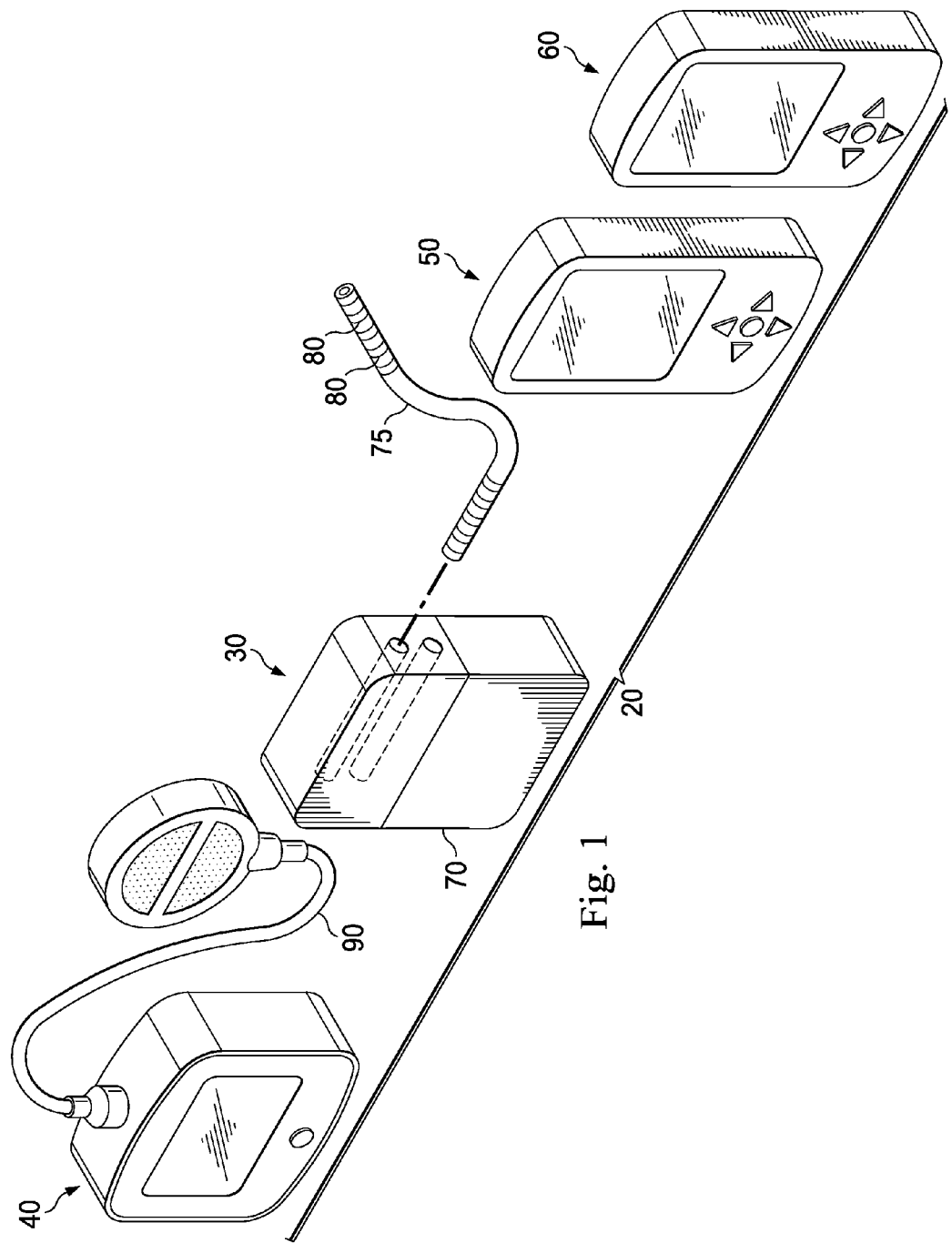
FIG. 1 is a simplified block diagram of an example medical system according to various aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

The use of active implanted medical devices has become increasingly prevalent over time. Some of these implanted medical devices include neurostimulator (also referred to as a pulse generator) devices that are capable of providing pain relief by delivering electrical stimulation to a patient. In that regards, electronic programmers have been used to configure or program these neurostimulators (or other types of suitable active implanted medical devices) so that they can be operated in a certain manner. These electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

In recent years, these electronic programmers have achieved significant improvements, for example, improvements in size, power consumption, lifetime, and ease of use. For instance, electronic programmers have been used to generate and/or display pain maps and stimulation maps (collectively referred to as sensation maps or medical maps) for a patient. In general, a pain map graphically illustrates the location or intensity of a patient's pain, and a stimulation map graphically illustrates the location or intensity of the electrical stimulation (e.g., stimulation delivered by the neurostimulator) perceived by the patient. These pain/stimulation maps can serve as useful tools for diagnosing the patient's pain and treatment and also allow visual/non-verbal communication between a patient and a healthcare professional. In addition, a history of the maps, if collected, can provide a record of a patient's treatment progress, and the maps can also be analyzed across patient groups. In some embodiments, to protect patient privacy, the personal information of the patients are stripped before the history of the pain/stimulation maps are collected and analyzed. In other words, the history of the pain/stimulation maps may be collected and analyzed anonymously in certain embodiments.

According to the present disclosure, image data used to graphically depict the pain/stimulation maps are pixelated (e.g., broken up into a number of irreducible pieces based on features of the image). Consequently, the data files associated with the pain/stimulation maps are typically contain a vast amount of data because of the large number of pixels required to represent the maps. In fact, map data files are generally too large to store in the limited storage capacity of an implanted medical device, such as an implantable neurostimulator. Existing neurostimulators only store the parameters of the electrical pulses being delivered to the patient (for example, frequency and amount of electrical current). Since implantable neurostimulators do not have sufficient storage capacity for the vast amount of data associated with the pain/stimulation maps, these maps (or associated data files) may have to be stored on external devices like stimulation parameter programmers or in an external database or library. Thus, the shortcomings of the present device and method of storing pain/stimulation maps are as follows:

- Patients and healthcare professionals have to coordinate the storage of the pain/stimulation maps, which is not only inconvenient and time-consuming, but it may also increase the likelihood that a pain map or stimulation map may be associated with a wrong patient.
- Healthcare professionals or patients in charge of the programmer containing the pain/stimulation maps might forget to bring the programmer to appointments.
- If a patient changes healthcare providers, the pain/stimulation maps are not automatically transferred to the new healthcare provider.
- Sharing medical maps requires transferring of a large amount of data, which may be a slow and frustrating process.
- The large file sizes of the pain/stimulation maps require an extensive storage capacity for the database or library in which they are stored, thereby increasing costs.

To address the issues discussed above, the present disclosure offers a method and system of compressing pain/stimulation maps down to a small enough size to facilitate their storage on an implanted medical device (e.g., implanted pulse generator), as discussed below in more detail.

FIG. 1 is a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

FIGS. 2-12 illustrate an embodiment of a user interface 100 implemented on an example clinician programmer 60. Specifically, the portions of the user interface 100 shown in FIGS. 2-12 illustrate the generation and display of a sensation map (e.g., a pain map or a stimulation map) according to the various aspects of the present disclosure. In some embodiments, the user interface 100 may be displayed on a screen of a programmer, for example a capacitive or resistive touch-sensitive display. In other embodiments, the user interface 100 may be displayed on a programmer and an external monitor simultaneously, for example in accordance with U.S. patent application Ser. No. 13/600,875, filed on Aug. 31, 2012, entitled "Clinician Programming System and Method", the disclosure of which is hereby incorporated by reference in its entirety. As such, both the healthcare provider (e.g., the target user of the user interface 100) and the patient are able to view the user interface at the same time.

Figure 2:
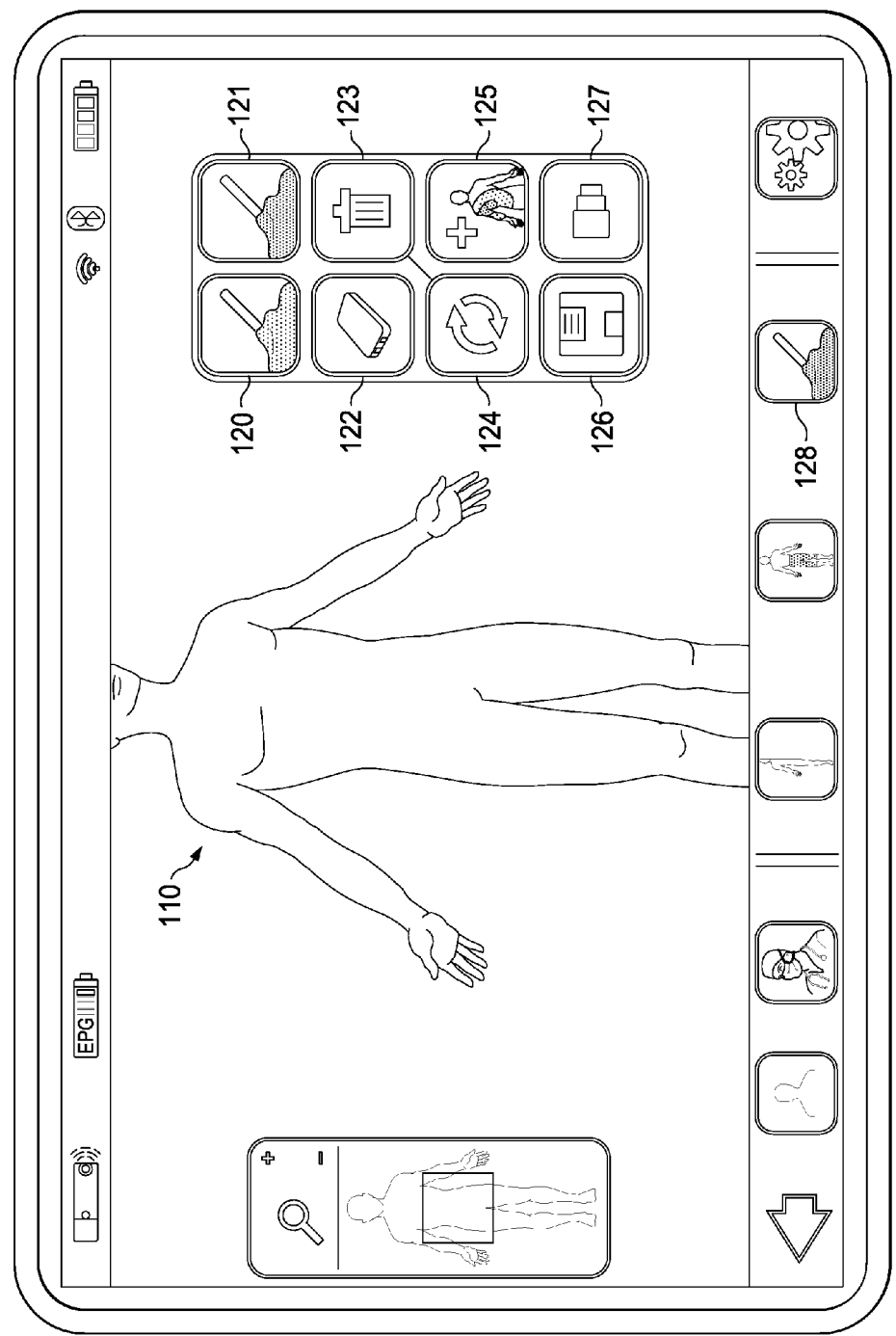
FIGS. 2, 3A-3B, 4A-4B, 5A-5B, and 6-12 illustrate embodiments of a user interface for generating, compressing, and sending a sensation map according to various aspects of the present disclosure.

Referring to FIG. 2, the user interface 100A illustrates a 3D model of a human body 110. The 3D human body model 110 includes an entire human body, though the user interface 100 may be configured to view only a portion of the human body model 110 at a time. The human body model 110 can also be moved in all directions, rotated, resized, or otherwise manipulated. In some embodiments, the human body model 110 is customized for a specific patient. For instance, if a patient is tall (e.g., 6 feet or taller), the human body model 110 may be created (or later resized) to be "taller" too, so as to correspond with the patient's height. As another example, if the patient is overweight or underweight, the human body model 110 may be created (or later resized) to be wider or narrower, so as to correspond with the patient's weight. As other examples, if the patient has particularly long or short limbs (or even missing limbs or body parts), hands/feet, or a specific body build, the human body model 110 may be created (or later resized) to correspond with these body characteristics of the patient as well.

In some embodiments, the present disclosure offers a database that includes a plurality of predefined human body models that each correspond to a specific body type, for example a predefined body type for a 40 year old Caucasian male with a height of 6'1 and a weight of 200 pounds, or a 20 year old African American female with a height of 5'5 with a weight of 120 pounds, so on and so forth. In these embodiments, a healthcare professional or the patient can quickly select a predefined body type from this database that most closely matches his/her physical conditions/characteristics. In this manner, the healthcare professional need not spend too much time specifically customizing the human body model 110 to the patient, since a predefined human body model that is substantially similar to the patient is already available from the database. It is also understood that such database may be available to a network of healthcare professionals and may be downloaded to the electronic programmer upon verifying the necessary login credentials. The patient models may also be uploaded from an electronic programmer to the database. In some further embodiments, the clinician programmer discussed herein is configured to capture an image of the patient (for example via an integrated camera). The proportions and other bodily details of the patient may then be automatically adjusted by processing the captured patient image.

Figure 3A:
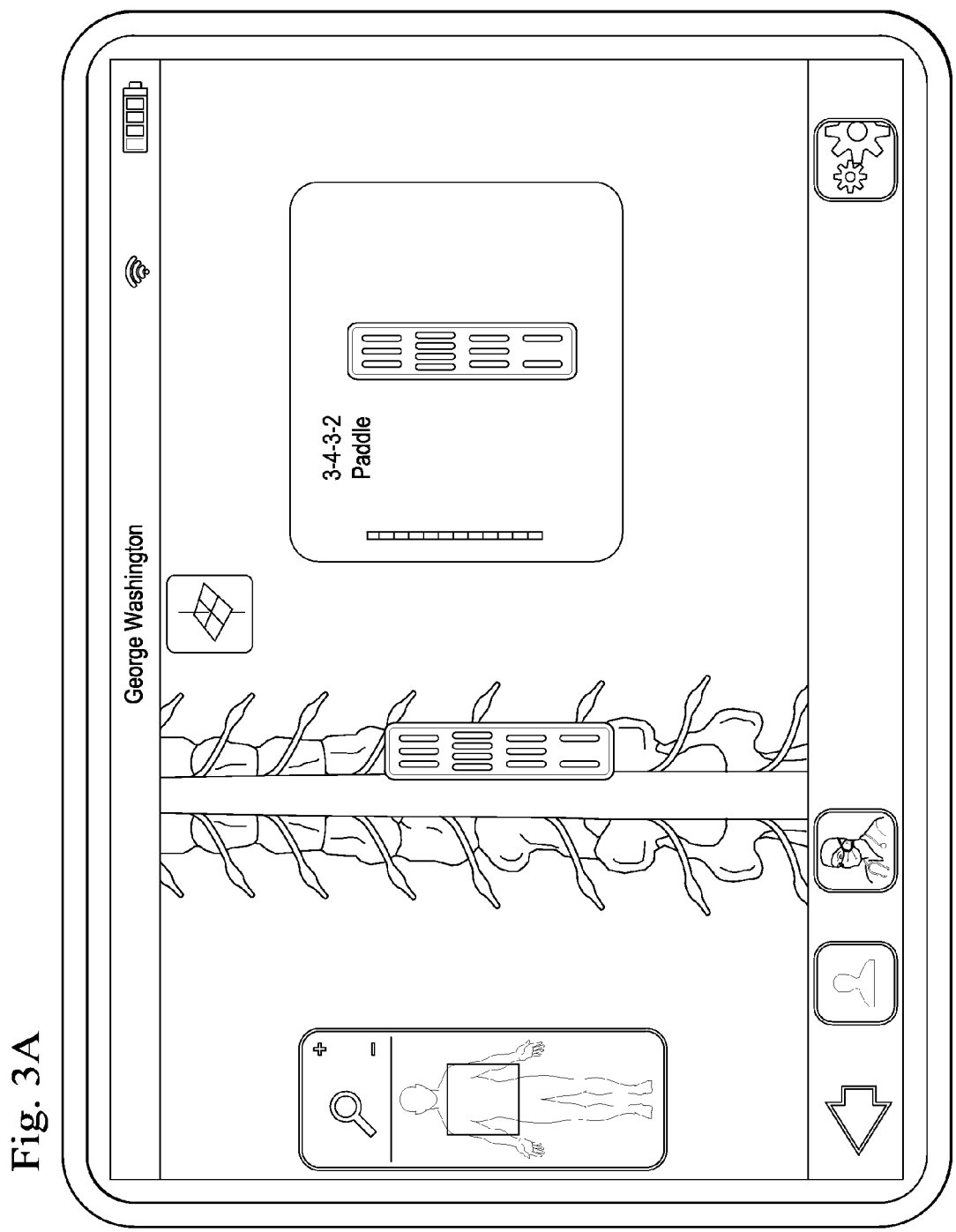
Figure 3B:
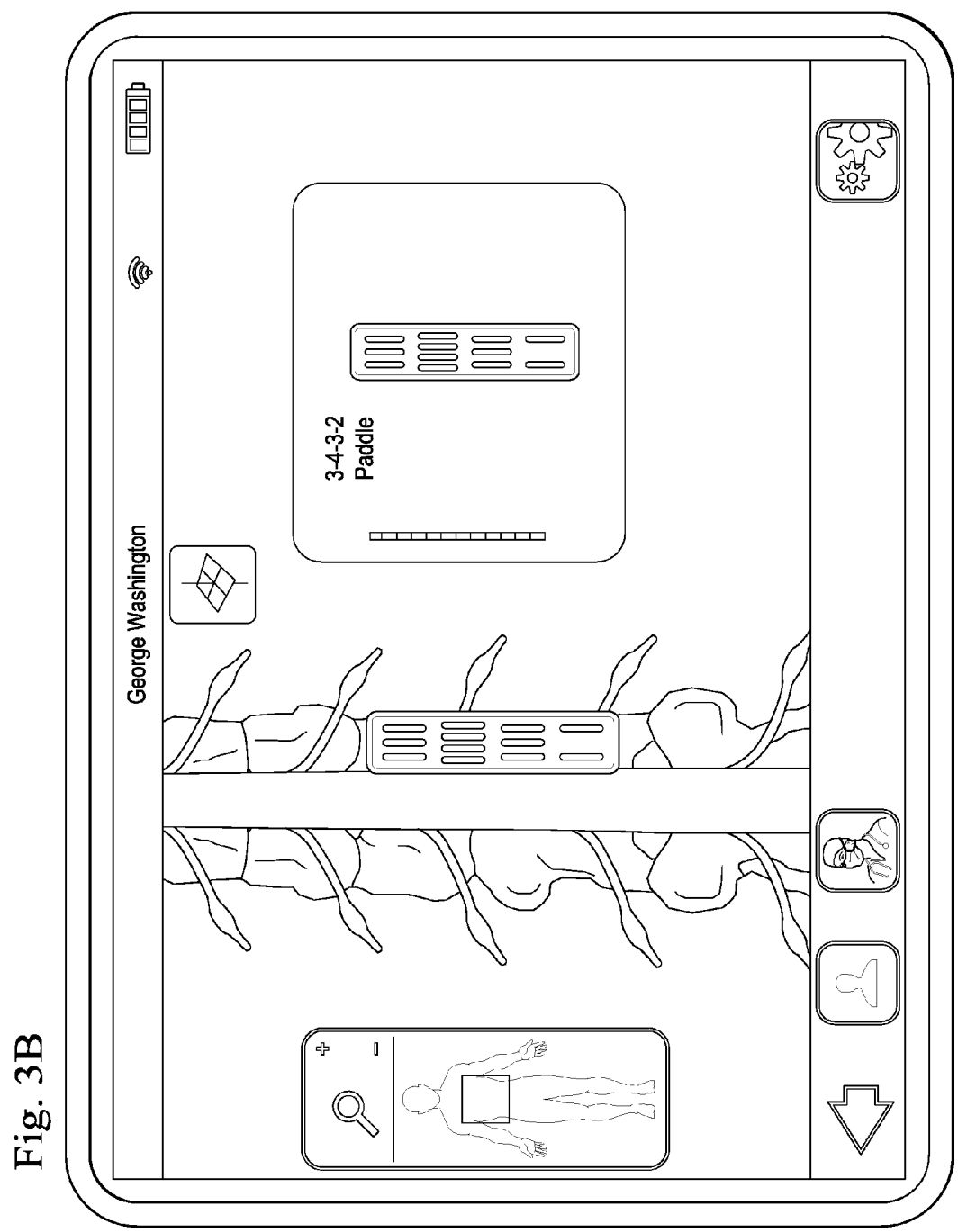

FIGS. 3A-3B, 4A-4B, 5A-5B, and 6-9 illustrate graphical examples illustrating how a human body model can be customized to more accurately match the physical traits of a patient. FIGS. 3A-3B are graphical illustrations of an implanted medical device (e.g., a paddle lead) relative to a spine of a patient. In FIG. 3A, the patient is a short patient, and therefore the implanted medical device covers more vertebra levels. In comparison, the patient is a tall patient in FIG. 3B, and thus the implanted medical device covers fewer vertebra levels. This is because the spacing between the vertebra levels increase as the patient's height increases, but the length of the implanted medical device will remain the same regardless of the patient's height. Thus, FIGS. 3A-3B highlight the importance of matching the actual patient with a model as closely as possible, as the efficacy of the treatment is dependent on the accurate modeling.

Figure 4A:
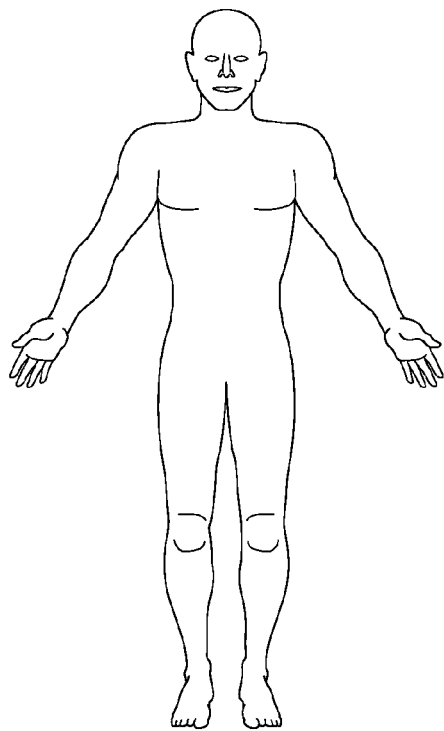
Figure 4B:
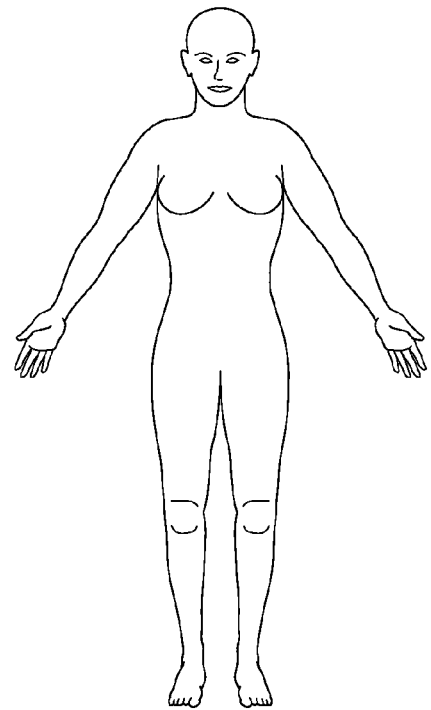
Figure 5A:
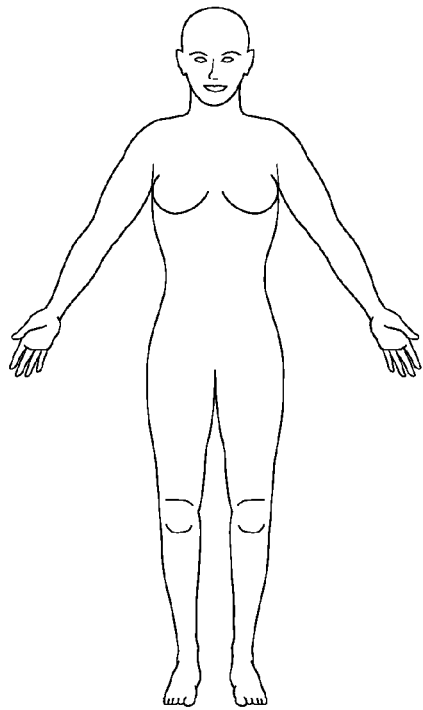
Figure 5B:
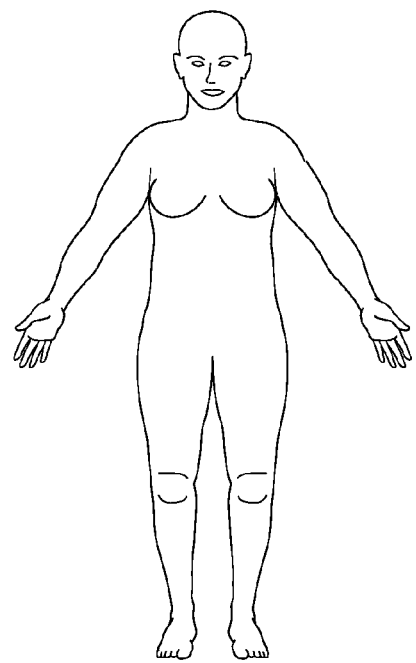
Figures 6, 7:
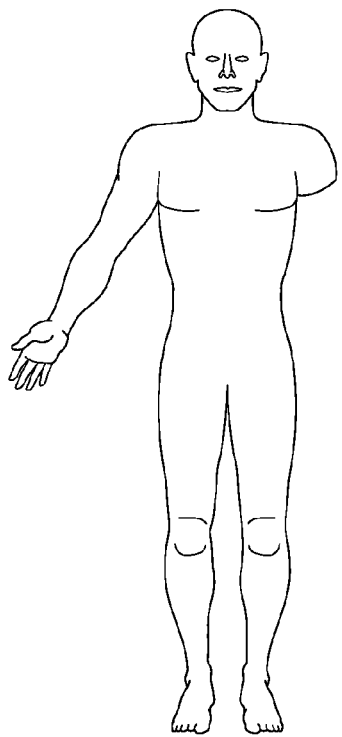
Figure 8:
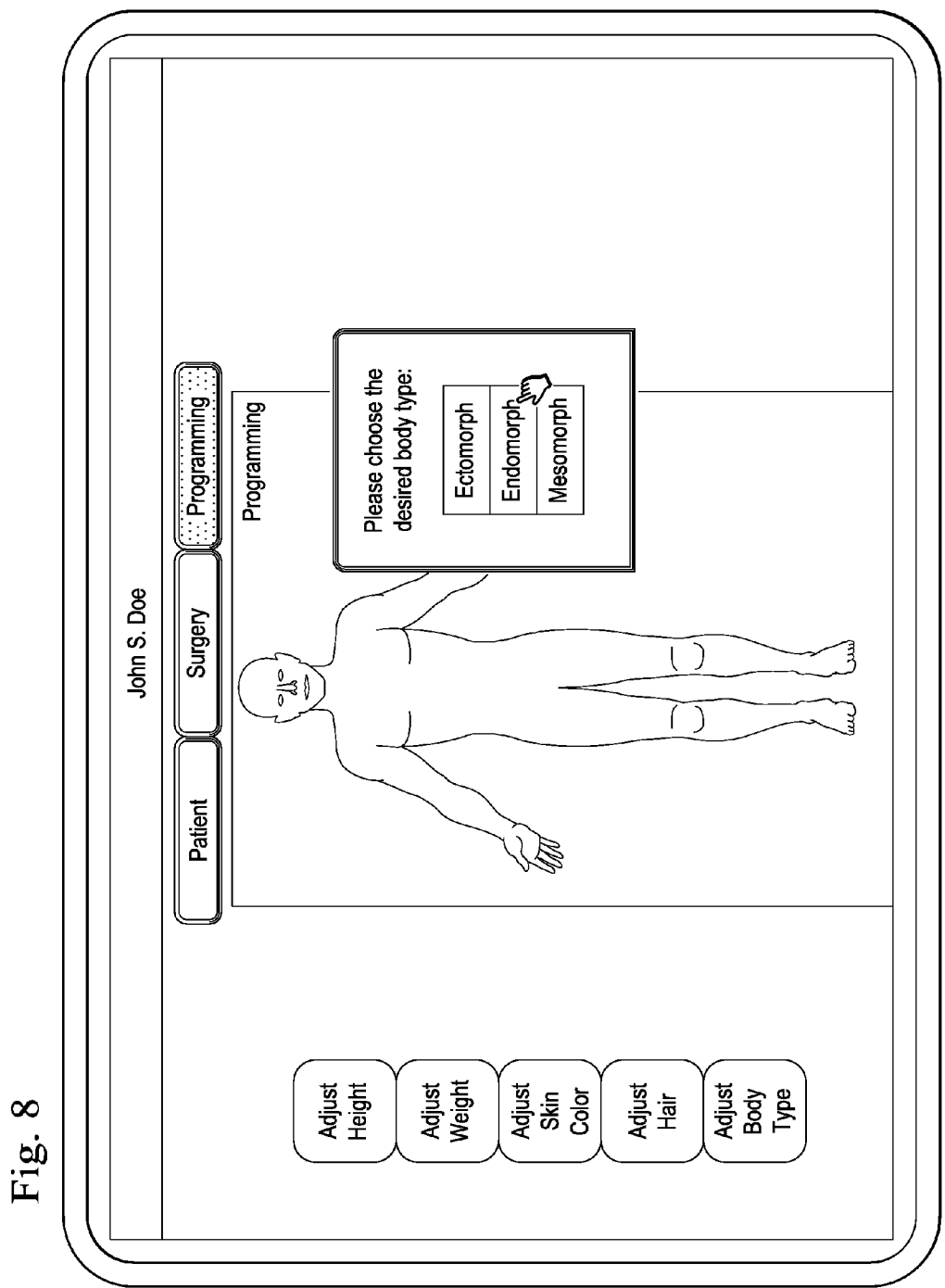

As discussed above, height is not the only variable that can be adjusted in customizing a human body model that closely matches the actual patient. Gender and weight are also among the variables that can be adjusted. As examples, FIG. 4A illustrates a standard male model, FIG. 4B illustrates a standard female model, FIG. 5A illustrates a tall and thin female model, and FIG. 5B illustrates a short and more heavy-set female model. Furthermore, another possible structural adjustment is the removal of appendages, which is illustrated in FIG. 6, where the model is missing a part of his left arm. The removal of appendages may be accomplished by not using all the vertices of the original model, for example. And although not specifically shown for reasons of simplicity, other variables that can be adjusted include skin color, hair color, eye color, etc.

Figure 9:
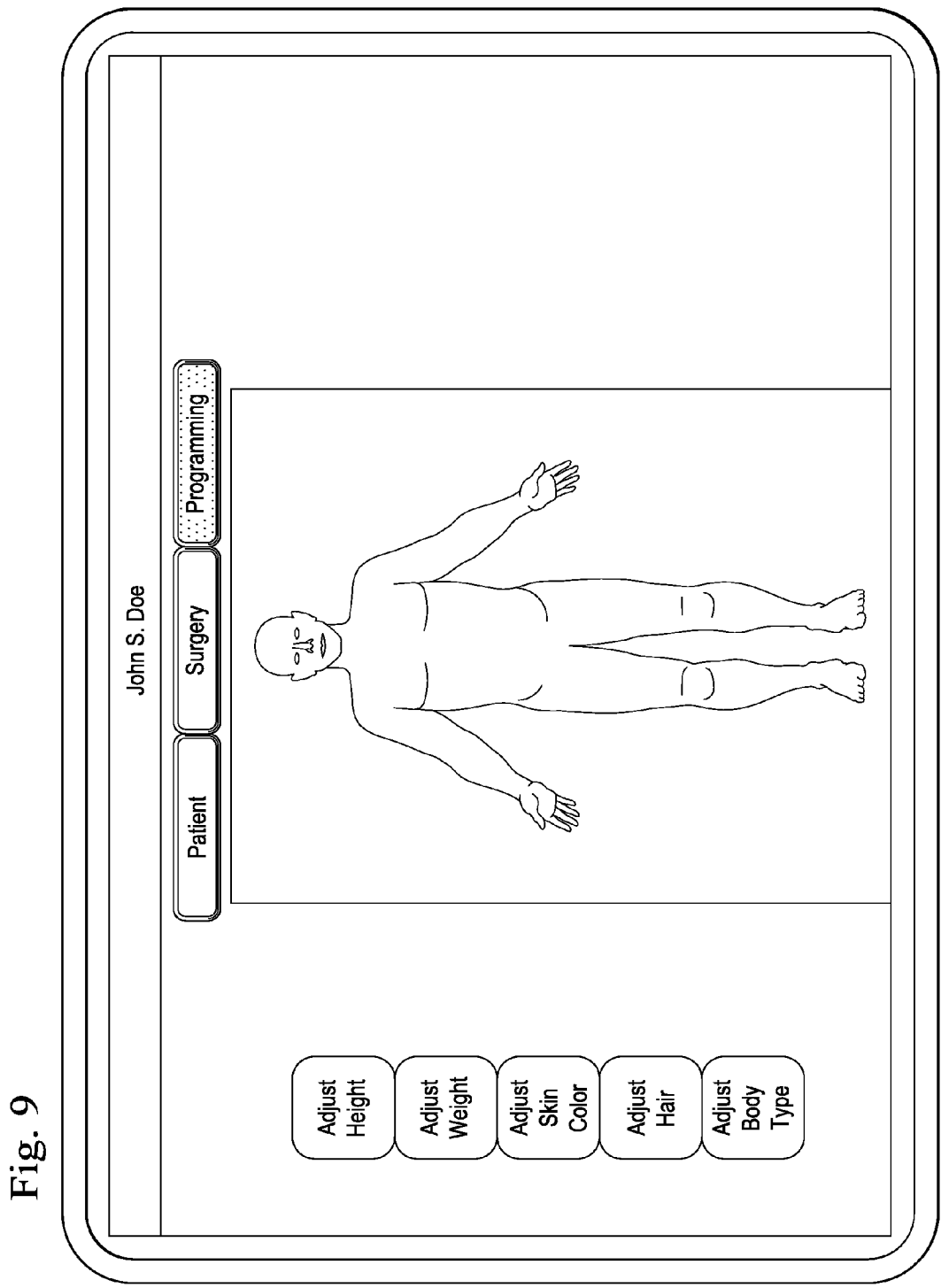

FIG. 7 is an example patient information record in which the user (who may or may not be the patient) may enter patient specifics such as height, weight, gender, body type, etc. discussed above. In some embodiments, the patient record may be used to automatically modify the human body model representing the actual patient. In other embodiments, the user may manually adjust the human body model manually. In yet other embodiments, the user may make manual adjustments to the human body model after a human body model has been automatically generated based on the patient information entered into the patient record. For example, in FIG. 8, a standard male model has been generated for patient "John S. Doe" based on the data entered into his patient record. The user wants to make further manual adjustments to the automatically-generated model, and thus a list of modification options appears, which includes "Adjust Height," "Adjust Weight," "Adjust Skin Color," "Adjust Hair," and "Adjust Body Type." The user wishes to make an adjustment to the body type and selects the option "Adjust Body Type." As a result, a list of body type options appears, which includes "Ectomorph" (heavy/rounded), "Endomorph" (lean), and "mesomorph" (muscular). Referring now to FIG. 9, an adjusted model is shown as a result of the user selecting "Ectomorph." Thus, the model is FIG. 9 is heavier and more rounded compared to the model in FIG. 8 before the adjustment. Of course, these adjustment options discussed above are merely examples, and additional adjustment options are envisioned in other embodiments.

Referring now back to FIG. 2, the user interface 100 also displays a plurality of menu items 120-127 to assist with the generation and display of the pain maps and stimulation maps (not visible in FIG. 2). The display of the menu items 120-127 is triggered by the user pressing on a virtual button 128. In the illustrated embodiment, the menu item 120 is used to generate a pain map or a stimulation map. After selecting the menu item 120, the patient can user his/her finger(s) as a simulated brush to draw or paint an area on the human body model 110 that corresponds to a region of pain the patient experiences. For example, if the patient feels pain in his/her shoulder, he/she can paint a pain map on the shoulder region of the human body model 110. The human body model 110 can also be rotated, so that the patient can paint the pain map in different regions of the human body model. The patient may revise the pain map to correspond as closely with the actual perceived regions of pain as possible. To facilitate the painting/drawing of the pain maps, the simulated brush may be of adjustable size.

The stimulation map may be created in a similar manner, except that the stimulation map corresponds with the perceived stimulation experienced by the patient. The pain map and stimulation map are drawn on a touch-sensitive screen in the illustrated embodiment. A graphics accelerator may be used to speed up the generation of these maps.

Once the virtual button 128 is engaged to trigger the display of the menu items 120-127, the menu items 120-121 may be used to indicate different levels of intensity of the pain or stimulation. For example, referring to FIG. 10, after the menu item 120 is used to create a "baseline" pain map that covers a region of the body in general, the menu item 121 (shown in FIG. 2) may be used to indicate a region where the pain is more intense. In the embodiment shown in FIG. 10, the patient may draw a region 140 as a "baseline" pain region to indicate general pain. This region 140 may represent the body regions where the patient feels some degree of pain. The patient may also draw a region 142 within the region 142 as an "intense" or "acute" pain region. In other words, the patient may feel much more pain in the region 142 than in the rest of the region 140. The degree of the pain intensity may correspond with a color (or hue) of the region, and a variety of colors may be available to represent different degrees of pain. Thus, a pain map of the present disclosure may reveal various regions with different degrees of pain. In some embodiments, the more painful regions are represented by darker colors, and the less painful regions are represented by lighter colors. The opposite may be true in other embodiments. In further embodiments, various pain maps may be created to represent different types of pain, for example a numbness, a burning pain, a tingling, a soreness, etc. These different types of pain may be represented by pain maps with different colors or different textures, for example. In yet other embodiments, the depth of pain (whether the pain is only skin-deep or penetrates to the muscle level) may also be represented by the pain maps, for example by different colors or different textures of the pain maps. It is also understood that the pain/stimulation maps may be resized proportionally to automatically correspond with the underlying human body model. That is, if the human body model on which the pain/stimulation maps are resized, the pain/stimulation maps may be resized accordingly.

Figure 10:
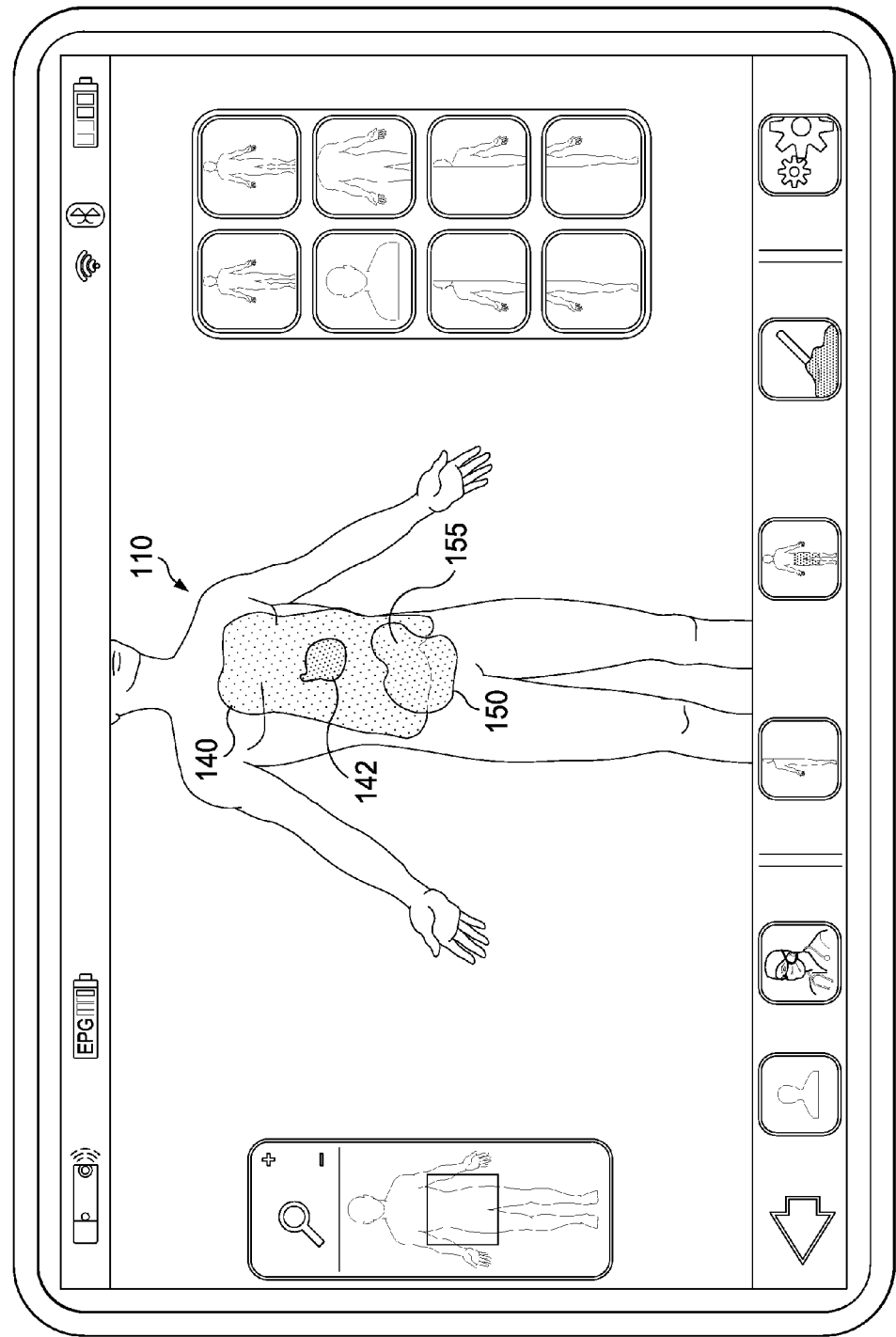

Similarly, the patient may also draw a region 150 to indicate a region on the body where the patient experiences stimulation while the stimulation therapy is active. The stimulation maps may be configured in a similar manner as the pain maps. In other words, the stimulation maps may be configured to portray different intensities of stimulation sensations, different regions of stimulation sensations, different types of stimulation sensations or different depths of stimulation sensations. Note that the pain region 140 and the stimulation region 150 may be displayed individually, or simultaneously, as shown in FIG. 10. An overlapping region 155 (an overlapping between the pain region 140 and the stimulation region 150) may also be displayed, which is helpful in helping the healthcare professional in diagnosing and treating the patient.

It is understood that although pain maps are used as an example herein for illustration purposes, stimulation maps containing regions with different stimulation intensity may be generated in the same manner.

Referring back to FIG. 2, the menu item 122 is used to erase or remove portions of the pain map or the stimulation map. This is done when the patient needs to revise an existing pain map or stimulation map, for example when the pain map or stimulation map is dated and no longer accurately reflects the patient's perceived pain or stimulation.

The menu item 123 is used to delete an existing pain map or stimulation map.

The menu item 124 is used to cycle through different maps, such as switching between pain maps and stimulation maps.

The menu item 125 is used to generate a new pain map or a new stimulation map.

The menu item 126 is used to save changes to a pain map or a stimulation map.

The menu item 127 is used to view a playback of the pain map and/or stimulation map associated with a patient. Among other things, this may be used to show progression of treatment.

Of course, these menu items 120-127 are merely examples. Some of these menu items may be removed, and other menu items may be added in alternative embodiments to carry out the generation and editing of the pain map and stimulation map.

The present disclosure also allows for predefined pain or stimulation regions. For example, referring now to FIG. 11, the user interface 100C shows a plurality of menu items 160-167 that each correspond to a predefined pain or stimulation region on the human body model 110. For example, in the embodiment shown, the menu item 160 may correspond to a predefined pain region in the right arm of the patient; the menu item 161 may correspond to a predefined pain region in the left arm of the patient; the menu item 162 may correspond to a predefined pain region in the waist and thighs of the patient; the menu item 163 may correspond to a predefined pain region in the abdomen of the patient; the menu item 164 may correspond to a predefined pain region in the right lower leg of the patient; the menu item 165 may correspond to a predefined pain region in the lower left leg of the patient; the menu item 166 may correspond to a predefined pain region in the right foot of the patient; and the menu item 167 may correspond to a predefined pain region in the left foot of the patient. In certain embodiments, the severity or intensity of pain/stimulation, type of pain/stimulation, and depth of pain/stimulation may be selected as a part of the predefined regions.

Figure 11:
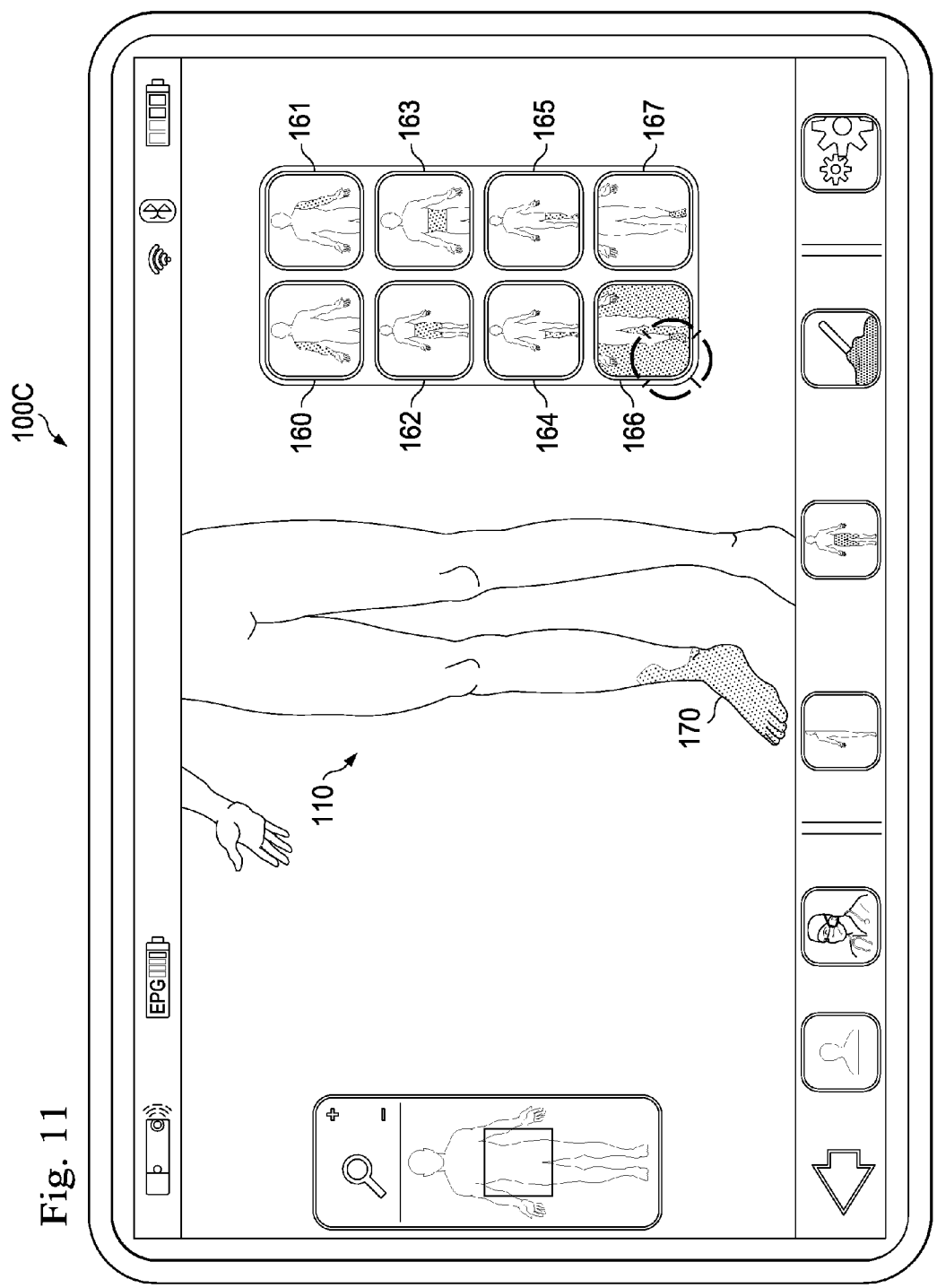
Figure 12:
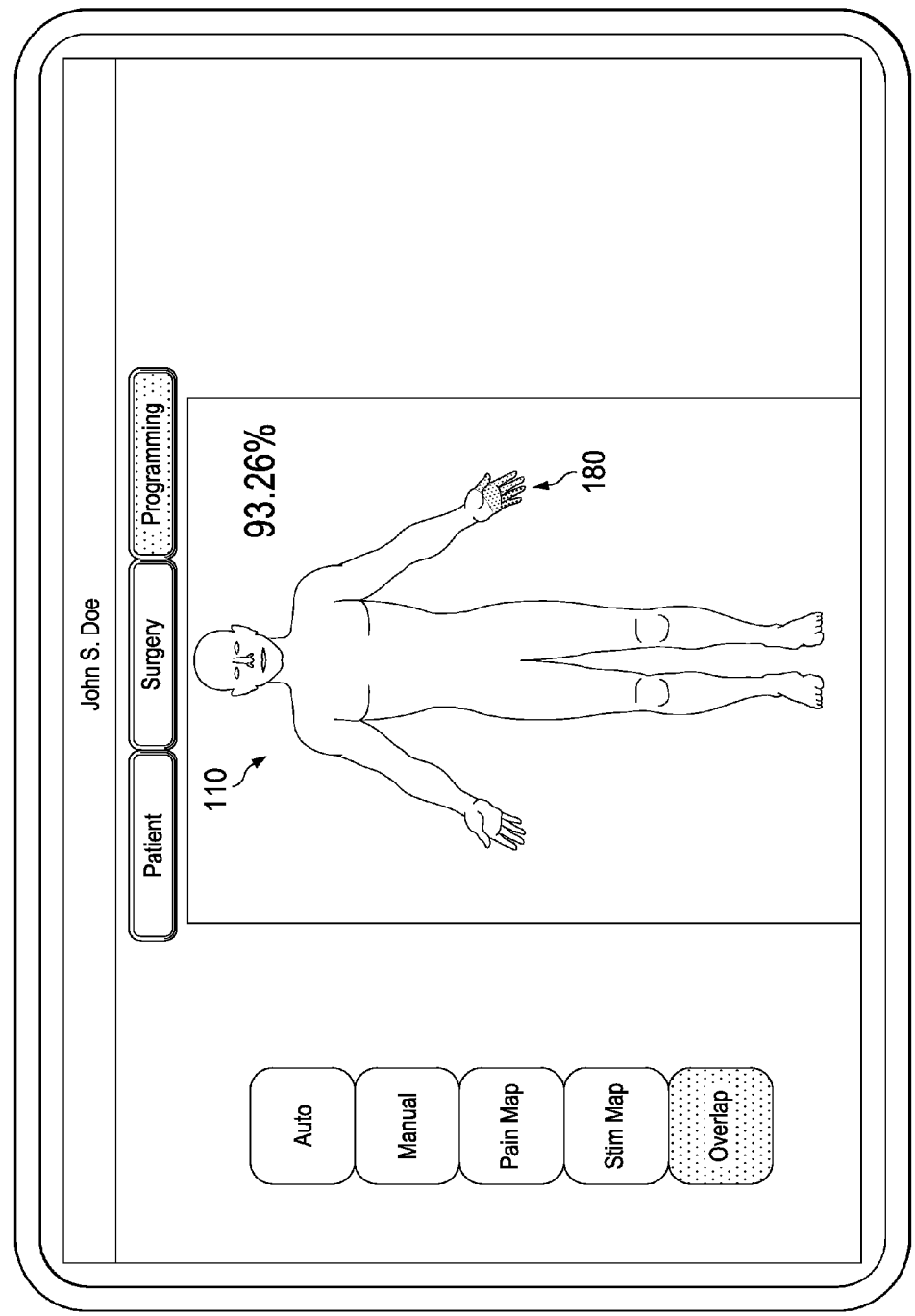

In the embodiment shown in FIG. 11, the menu item 166 is selected, which automatically generates a pain region 170 that covers the right foot of the human body model 110. The pain region 170 can then be revised by the patient to create a pain map that more accurately matches with the pain experienced by the patient. In the same manner, a predefined stimulation region may be automatically generated and then revised to create a desired stimulation map.

The correlations between stimulation parameters (e.g., milliamps, polarity, pulse width, frequency, lead position) or activity parameters (e.g., sitting, standing, sleeping, running, etc.) and perceived stimulation maps are a valuable part of map analysis, because they indicate the degree to which a parameter is related to a certain effect. Map correlations, which can be carried out between individual stimulation programs ("programs") and effective or perceived stimulation maps, are also possible between groups of programs ("programs sets") and an effective stimulation map. A more detailed discussion of stimulation parameters, programs and program sets is found in U.S. patent application Ser. No. 13/601,631, filed on Aug. 31, 2012, and entitled "Programming and Virtual Reality Representation of Stimulation Parameter Groups" to Norbert Kaula, et al., the content of which is hereby incorporated by reference in its entirety. Note that in some embodiments, the "program sets" may also be referred to as "programs" while the "programs" may be referred to as "sub-programs."

The present disclosure further allows for a determination of an overlap between a pain map and a stimulation map. For example, referring now to FIG. 12, after a pain map and a stimulation map have been generated, the user interface 100D can be used to determine an overlap 180 between the pain map and the stimulation map. The overlap may vary as a percentage from 0% to 100%. In some embodiments, or even greater than 100% in other embodiments For example, if the pain map covers an abdominal region, and the stimulation map covers the abdominal region as well as a chest region, then the overlap may be considered to be greater than 100%. It may be desirable to have a close match between the pain map and the stimulation map, as that may indicate an optimal and efficient stimulation of the pain regions for the patient. For purposes of providing an example, the overlap between the pain and stimulation maps is computed to be at 93.26% in the embodiment shown. In addition, the pain and stimulation maps may be weighted differently, for example by using a slider tool (not illustrated herein), with a readout of the weights. There may be two different types of weights. One weight is to use the slider tool to visually indicate the differences between the pain areas and the stimulation areas. The slider tool may be used to fade in and out of the two types of maps (i.e., pain map and stimulation map) while they are overlapped. The region of overlap may be represented by a different color from either of the maps. Another weight is to show areas of the model that are more important for pain management. In addition, the user interface may also indicate areas of stimulation that are not overlapping a pain area. Such areas of stimulation are unnecessary and may cause discomfort for the patient. In some embodiments, the "extra" stimulation areas are shown on the map and may also be accompanied by a "+" sign next to the percentage. Alternatively, the user interface may be configured to only display areas of pain and/or stimulation that are outside the overlapped area between pain map and stimulation map. The degree of non-overlapped areas may also be indicated by a percentage number.

In various embodiments, any of the maps in Table 1 below may be compared, either one to another, or in combinations. The possibilities range from maps recorded at the initial session through the current session, and include pain maps (PAIN); stimulation program maps (STIM-Px), where x may vary up to a predetermined number (e.g. 4); and stimulation program set maps (STIM-Sx), where y is determined by the number of programs (x).

For example, if there are three stimulation programs (STIM-P1, STIM-P2, STIM-P3), then there are seven possible stimulation program sets (STIM-P1, STIM-P2, STIM-P3, STIM-P1+STIM-P2, STIM-P1+STIM-P3, STIM-P2+STIM-P3, STIM-P1+STIM-P2+STIM-P3).

TABLE 1

| Map List | | |
|---|---|---|
| $PAIN_{init}$ | ... | $PAIN_{curr}$ |
| $STIM\text{-}Px_{init}$* | ... | $STIM\text{-}Px_{curr}$ |
| $STIM\text{-}Sy_{init}$* | ... | $STIM\text{-}Sy_{curr}$ |

*Each stimulation category includes subcategories corresponding to stimulation and the activity parameters discussed above.

Additional aspects of the generation and display of the pain/stimulation maps are discussed in provisional U.S. Patent Application No. 61/824,296, filed on May 16, 2013, entitled "Features and Functionalities of an Advanced Clinician Programmer," which as discussed above has been incorporated by reference in its entirety.

Based on the discussions above, it can be seen that the pain/stimulation maps of the present disclosure may be data-heavy, particularly since they may contain 3D information (e.g., the maps may be generated over a 3D model). Meanwhile, implantable medical devices such as IPGs (an example of a neurostimulator) typically have limited data storage capacity. The limited data storage capacity is due at least in part to the small physical dimensions, the access speed requirements, and power consumption constraints of the implantable medical device. Therefore, the large file sizes associated with the 3D pain/stimulation maps make their storage on the IPG (associated with the patient for whom the pain/stimulation maps are generated) impractical, if not impossible. Thus, the present disclosure utilizes a compression process to reduce the data sizes of the pain/stimulation maps. The compressed pain/stimulation maps may then be sent to the IPG of the patient.

As a first step of the data compression, a technique known as Connected Component Labeling (CCL) is used to determine areas of interest on the pain/stimulation maps. In one aspect, Connected Component Labeling identifies regions of pixels that have similar or identical qualities (for example, color). These regions are also called "blobs." Blobs can usually be described with less information than can the original pixelated images. After Connected Component Labeling is performed to the pain/stimulation maps, and the areas of interest are identified, a plurality of compression methods or techniques is executed on the pain/stimulation maps. As an example, a "contour tracing" method may be executed on the pain/stimulation map. In general, contour tracing is a method that identifies the edges or borders of a blob. Several types of contour tracing are described below for compression of medical map data, though other types exist and can be used.

Chain Code: Represent a contour/boundary by a connected set of straight-line segments whose length and direction are specified.

Minimum Perimeter Polygon: Represent the boundary of a blob by a polygon whose sides are segments of the boundary.

Fourier Descriptors: Define a boundary by set of points whose coordinate (location) data have been reduced.

Estimation With Primitives: Approximate a boundary with a set of sides or arcs from primitive shapes such as lines, circles, and ellipses.

In addition to contour tracing, other types of data compression methods may include, but are not limited to, Run-Length Encoding, Huffman coding, Golomb coding, Arithmetic coding, LZW coding, Symbol-based coding, and bit-plane coding, etc.

The pain/stimulation maps are compressed by each of the plurality of suitable data compression methods, and a respective compressed data file is generated accordingly for each compression method. One of these compressed data files may then be selected for storage on the IPG of the patient. For example, the compressed data file having the smallest data size may be selected for storage. This may be repeated for each of the pain/stimulation maps, thereby generating a plurality of available compressed data files suitable for storage on the IPG. Note that each compressed data file need not necessarily be associated with only one compression technique. Instead, multiple compression techniques may be associated with a single data file. For example, a pain/stimulation map for which a data file is generated may have a plurality of different segments with unique graphical characteristics. For example, the pain/stimulation map may have different types/depths of pain/stimulation that are represented by different textures. In addition, various pain/stimulation maps may be generated on different body regions that have different geometries. Due to these differences, one compression technique may be more suitable for compressing one body region or one particular pain/stimulation map, while another compression technique may be more suitable for compressing another body region or another pain/stimulation map. Consequently, a given compressed data file may be generated by the application of several different compression techniques.

A clinician programmer such as the clinician programmer 60 in FIG. 1 may be used to perform the compression process discussed above with respect to the pain/stimulation maps. The clinician programmer 60 is also used to establish a communication channel with the IPG (e.g. the IPG 70 in FIG. 1) and then transfer the compressed data files to the IPG. In some embodiments, in addition to or instead of storage on the IPG, the compressed data files may be sent to an external database (e.g., an electronic database residing on one or more remote computer servers) for storage. While these compressed data files are small in size, they contain enough information that can be used to reconstruct the original pain/stimulation maps (i.e., uncompressed pain/stimulation maps). Thus, at a later point in time, these compressed data files may be retrieved (e.g., by a clinician programmer) whenever necessary to reconstruct the pain/stimulation maps. To properly reconstruct the pain/stimulation maps, the stored data needs to contain whatever compression technique was used, so that the same method or technique can be used to reverse the process (i.e., reconstruction). In other embodiments, the compressed data files may be sent to an external pulse generator (EPG) or another medical component in the neurostimulation system for storage.

In some embodiments, the IPG may contain a partitionable memory storage, for example in accordance with the IPG disclosed in U.S. patent application Ser. No. 13/604,197, filed on Sep. 5, 2012, entitled "Method and System for Associating Patient Records with Pulse Generators," the disclosure of which is hereby incorporated by reference in its entirety. In other words, the memory for the IPG may be divided or separated into a plurality of different mutually exclusive partitions. The data stored in one of the partitions may be inaccessible by entities that also store data in the other partition. Different types of data may be stored in these different partitions. For example, one of the memory partitions may be configured to store personal information of a patient in which the IPG is implanted. The personal information may include visual identification information of the patient. Such visual identification information may include an electronic photograph or picture of the patient, or an electronic video of the patient. The personal information of the patient may also include other types of biometric, demographic, or biographical data of the patient, such as the name, residential address, email address, employment, phone number, birthdate, age, height, weight, blood type, medication taken, symptoms, and hospital identification number of the patient, etc.

In comparison, the other memory partition may be configured to store one or more compressed data files that allow for the reconstruction of the pain/stimulation maps as discussed above, as well as treatment protocols. The treatment protocol may include one or more of the following: a date of sensation map creation, a type of implant lead (e.g., 1×12, 2×6, etc.) containing electrodes configured to deliver electrical stimulation to the patient, an activated electrode configuration (e.g., which electrodes are programmed to be an anode or a cathode) on the implant lead, a polarity programmed for each activated electrode, an amount of current programmed for each activated electrode, a pulse width programmed for each activated electrode, and a frequency programmed for each activated electrode. Each compressed data file may be associated with a respective treatment protocol. The compressed data file and the treatment protocol may be downloaded from the clinician programmer via an established electronic communications link.

In some embodiments, the clinician programmer may generate a plurality of pain/stimulation maps over a period of time, where each of the pain/stimulation maps is generated at a different point in time. For example, a first pain map and a first stimulation map may be generated on Jan. 10, 2008, a second pain map and a second stimulation map may be generated on Jan. 10, 2009, a third pain map and a third stimulation map may be generated on Jan. 10, 2010, and a fourth pain map and a fourth stimulation map may be generated on Jan. 10, 2011. The clinician programmer can compress all of these pain/stimulation maps and generate the compressed data files in the manner discussed above. Each of the compressed data files may also contain the time information (i.e., the time that the pain/stimulation map is generated). The clinician programmer then sends all the compressed data files to the IPG for storage. At a later point in time, these compressed data files may be retrieved by another clinician programmer (or another suitable device) and may be used to reconstruct their corresponding pain/stimulation maps. As such, a history of pain/stimulation maps may be stored in the IPG and may be retrieved at any time. A healthcare professional may then use this history of pain/stimulation maps and see how the patient's pain has migrated or changed over time, and how effective the stimulation therapy is at these different points in time. In some embodiments, the IPG may be configured to store a record of the compressed data files, so that even after the data files are erased, a record of their storage on the IPG may still be retrieved. Again, multiple compression mechanisms may be used to compress data across multiple files. Whichever method that offers the best results will be used. Since each file contains the information regarding which method was used to carry out the compression, decompression can be done using the same method.

In some embodiments, the memory storage capacity on the IPG may not be sufficiently big to hold even several of the compressed data files. For example, it may not be big enough to hold 4 compressed data files. In that case, the IPG and the clinician programmer may be configured to let the memory storage of the IPG to automatically store data files that will fit and discard one or more data files that will not fit. For example, data files 2, 3, 4 may be stored, but data file 1 will be discarded. In some embodiments, the user may be presented with an option so he can choose whichever data file he wishes to save to the IPG.

The embodiments of the present disclosure offer are many advantages by allowing compressed pain/stimulation maps to be stored on the IPG. It is understood, however, that not all advantages are necessarily discussed herein, other embodiments may offer different advantages, and that no advantage is required for all embodiments. Some of these advantages are associated with the fact that IPGs are implanted in the patient, and as such they are always with the patient. Thus, the compressed pain/stimulation maps are stored in a reliable place (i.e., the patient's body) and may be readily retrieved wherever the patient goes.

Various shortcomings of previous methods and the advantages offered by the embodiments disclosed herein are listed below:

Problem: Patients and providers have to coordinate the storage of the pain/stimulation maps.

Advantage: Pain/stimulation maps are stored on the IPG, so no coordination is necessary.

Problem: Healthcare professionals or patients in charge of the programmer containing the pain/stimulation maps might forget to bring the programmer to appointments.

Advantage: The IPG is implanted in the patient, so the pain/stimulation maps will always be available at the appointments.

Problem: If a patient changes providers, pain/stimulation maps are not automatically transferred to the new provider.

Advantage: The new provider can readily access the pain/stimulation maps since they are stored on the IPG implanted inside the patient.

Problem: Sharing pain/stimulation maps requires transferring data from the device used to record the pain/stimulation map to another device or database.

Advantage: Users with devices capable of communicating with the IPG can download the pain/stimulation maps.

Problem: Uncompressed pain/stimulation maps have large data sizes, which require large databases. The larger the database, the larger the cost of the storage space.

Advantage: Pain/stimulation maps are compressed into small data files that can be used to reconstruct the original pain/stimulation maps. The storage of small compressed data files reduce needed storage space.

Problem: Adding uncompressed pain/stimulation maps to the database requires transferring a large amount of data to the database, which may take a long time.

Advantage: Using smaller compressed data files allows shorter transfer times.

Figure 13:
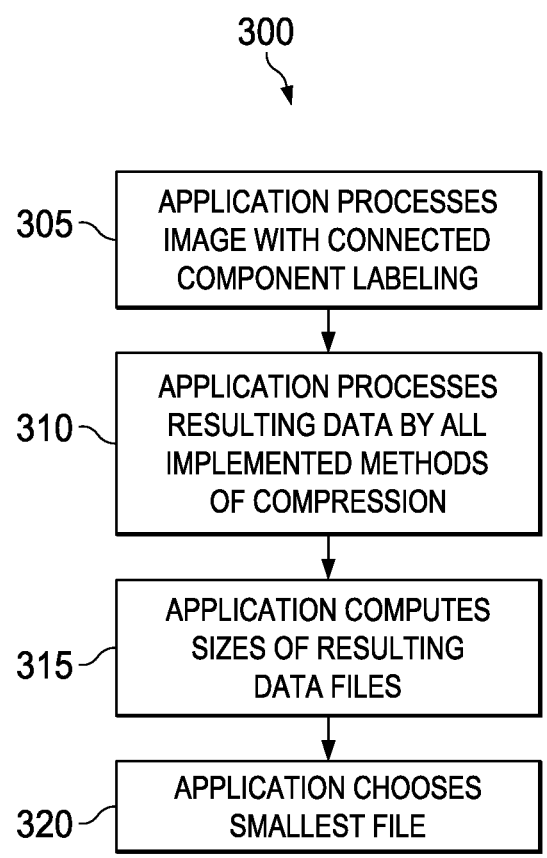
FIG. 13 is a simplified flowchart illustrating a method of compressing a sensation map according to various aspects of the present disclosure.

FIG. 13 is a simplified flowchart of a method 300 of compressing a pain/stimulation map according to the various aspects of the present disclosure. The method 300 includes a step 305, in which an application on a clinician programmer processes an image with Connected Component Labeling. In some embodiments, the image includes a pain map or a stimulation map. The method 300 proceeds to a step 310, in which the application of the clinician programmer processes the resulting data (i.e., data obtained from the step 305) by a plurality of compression methods. These compression methods may include various contour tracing methods such as chain code, minimum perimeter polygon, Fourier descriptors, or estimation with primitives. A plurality of data files are obtained by performing the step 310. The method 300 then continues to step 315, in which the application on the clinician programmer computes the sizes of the data files obtained from the step 310. The method 300 then proceeds to step 320, in which the application on the clinician programmer chooses the smallest data file. The method 300 may include additional steps not illustrated in FIG. 13. For example, the data file chosen in step 320 may then be sent to an implanted medical device such as an IPG for storage.

Figure 14:
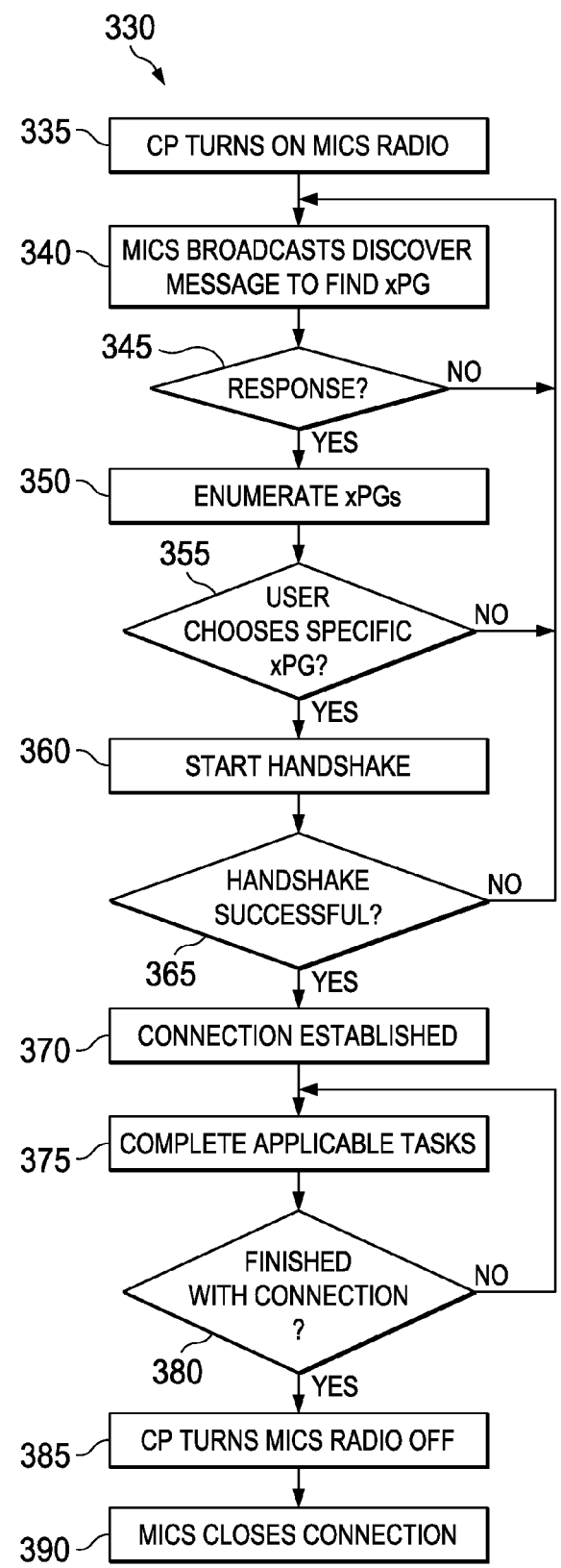
FIG. 14 is a simplified flowchart illustrating a method of establishing a connection with an implanted medical device according to various aspects of the present disclosure.

FIG. 14 is a simplified flowchart of a method 330 of communication between a clinician programmer and a pulse generator according to the various aspects of the present disclosure. The method 330 includes a step 335, in which a clinician programmer turns on a radio. The radio may be a radio operating under the Medical Implant Communication Services (MICS) protocol. The method 330 includes a step 340, in which the MICS radio broadcasts a discover message to find a pulse generator, which could be an IPG or an EPG. The method 330 includes a decision step 345 to determine if there is a response. If the answer is yes, the method 330 proceeds to step 350 to enumerate the pulse generators. In the answer is no, the method 330 repeats the step 340 again. The method 330 includes a decision step 355 to determine if the user chose a specific pulse generator. If the answer from the decision step 355 is yes, the method 330 proceeds to step 360 to start a handshake process, which is a process used to establish a connection. If the answer from the decision step 355 is no, the method 330 repeats the step 340 again. The method 330 includes a decision step 365 to determine if the handshake is successful. If the answer from the decision step 365 is yes, then the method 330 proceeds to step 370 in which a connection is established. If the answer from the decision step 365 is no, then the method 330 repeats the step 340 again. The method 330 includes a step 375, in which applicable tasks are completed after the connection is established in the step 370. In some embodiments, the applicable tasks refer to the transfer of the compressed map data files from the clinician programmer to the pulse generator. The method 330 then continues to a decision step 380 to determine whether the connection is finished. If the answer from the decision step 380 is yes, the method 330 proceeds to step 385 in which the clinician programmer turns the MICS radio off. If the answer from the decision 380 is nom, the method 330 repeats the step 375 again. The method 330 then concludes with a step 390 in which the MICS connection is closed.

Figure 15A:
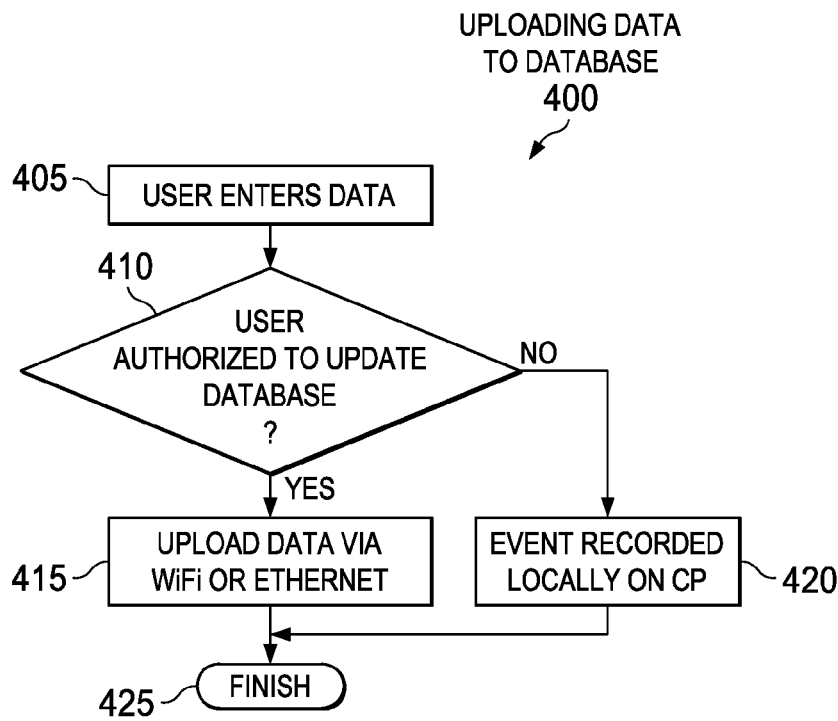
FIGS. 15A and 15B are simplified flowcharts illustrating methods of conducting communications between an electronic programmer and a remote database according to various aspects of the present disclosure.
Figure 15B:
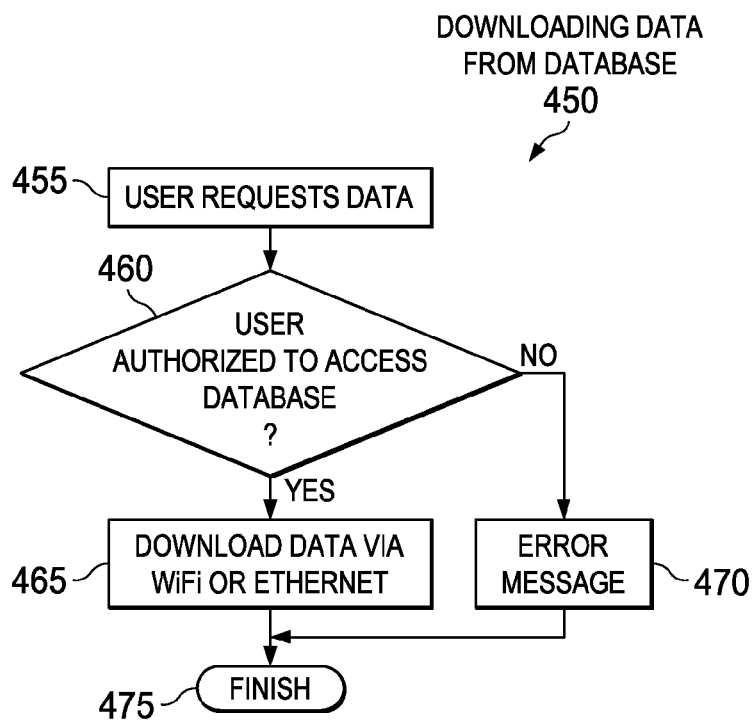

FIGS. 15A-15B are flowcharts of simplified example methods 400 and 450 that illustrate the process of communication between a healthcare professional (i.e., the user) using the clinician programmer (as an embodiment of the electronic programmer discussed above) and a remote database. Referring first to FIG. 15A, the method 400 pertains to the uploading of data from the clinician programmer to the database. The method 400 includes step 405 in which the user enters data. Next, a decision step 410 determines whether the user is authorized to update the database. If the answer is yes, then the database is updated in step 415 by uploading data via a wireless or wired network, such as Wi-Fi or Ethernet. If the user is not authorized to update the database, the method 400 proceeds to step 420, where the attempted update event is recorded locally on the clinician programmer. The method 400 thereafter finishes in step 425.

Referring first to FIG. 15B, the method 450 pertains to the downloading of data from the database to the clinician programmer. The method 400 includes step 455 in which the user requests data. Next, a decision step 460 determines whether the user is authorized to access the database. If the answer is yes, then the database is accessed in step 465 and the requested data is downloaded via a wireless or wired network, such as WiFi or Ethernet. If the user is not authorized to access the database, the method 450 proceeds to step 470, where an error message is displayed on the clinician programmer. The method 450 thereafter finishes in step 475.

Figure 16:
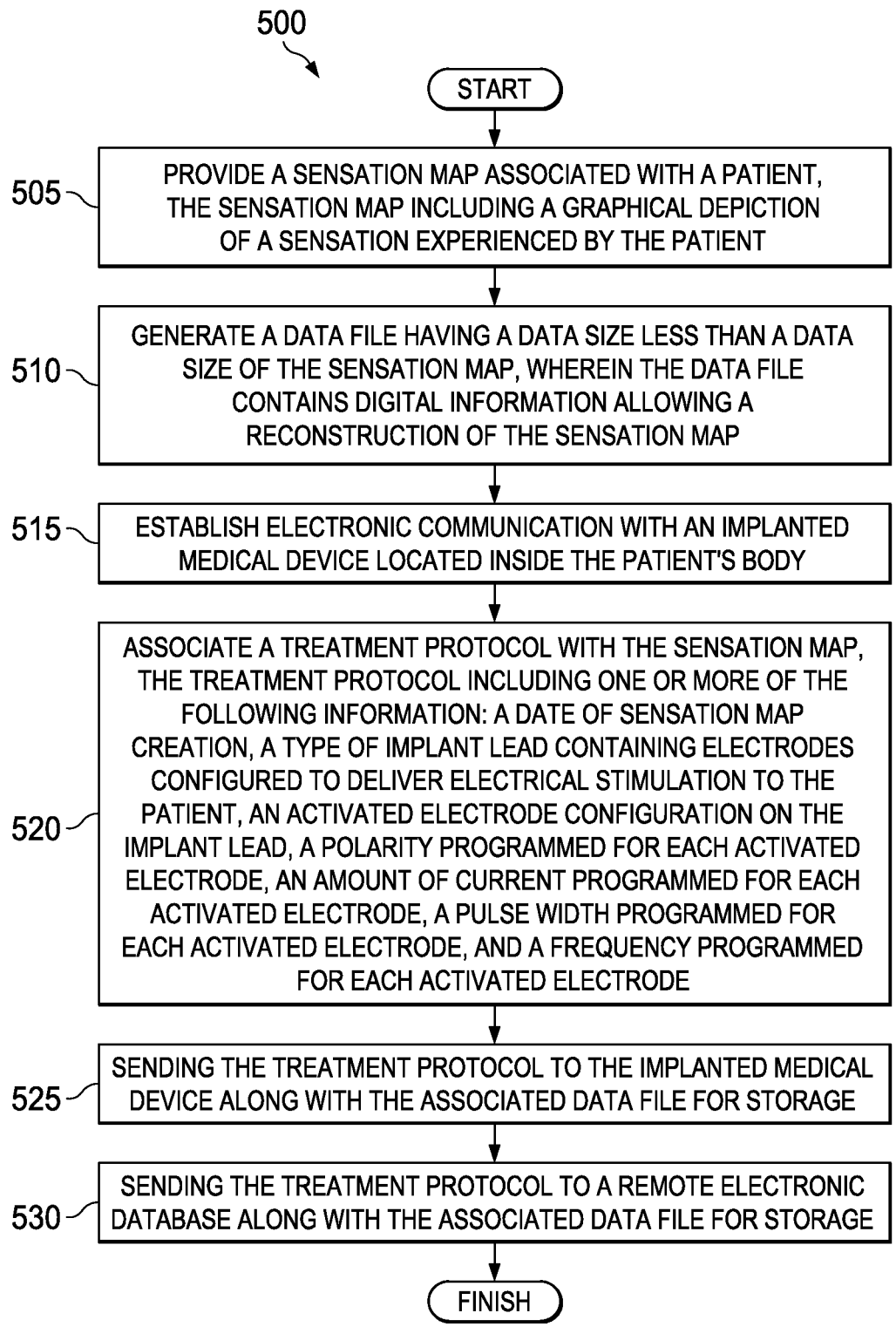
FIG. 16 is a simplified flowchart illustrating a method of storing a sensation map according to various aspects of the present disclosure.

FIG. 16 is a simplified flowchart of a method 500 of compressing and sending a sensation map according to various aspects of the present disclosure. The method 500 may be performed by a clinician programmer having a touch-sensitive user interface. The method 500 includes a step 505, in which a sensation map associated with a patient is provided. The sensation may be a pain sensation or a stimulation sensation (e.g., paresthesia). The sensation map includes a graphical depiction of a sensation experienced by the patient. The graphical depiction of the pain or stimulation is displayed through the graphical user interface. In some embodiments, the sensation map is generated over a three-dimensional (3D) human body model. In some embodiments, the 3D human body model is customized to the patient based on physical characteristics of the patient that include one or more of the following: height, weight, age, gender, and ethnicity The method 500 includes a step 510, in which a data file is generated. The data file has a data size less than a data size of the sensation map. The data file contains digital information allowing a reconstruction of the sensation map. In some embodiments, the step 510 includes the following steps: performing a Connected Component Labeling (CCL) process to the sensation map to generate a processed image of the sensation map; generating a plurality of data files by executing a plurality of data compression algorithms to the processed image of the sensation map, respectively, the data compression algorithms being selected from the group consisting of: Chain Code, Minimum Perimeter Polygon, Estimation with Primitives, Fourier descriptors, and run-length encoding; computing a respective data size for each of the data files; and selecting the data file with a smallest data size as the data file to be sent to the implanted medical device.

The method 500 includes a step 515, in which electronic communication is established with an implanted medical device located inside the patient's body. In some embodiments, the implanted medical device is an IPG. The electronic communication may be established through radios of the clinician programmer and the implanted medical device under the MICS protocol.

The method 500 includes a step 520, in which a treatment protocol is associated with the sensation map. In some embodiments, the treatment protocol includes one or more of the following information: a date of sensation map creation, a type of implant lead containing electrodes configured to deliver electrical stimulation to the patient, an activated electrode configuration on the implant lead, a polarity programmed for each activated electrode, an amount of current programmed for each activated electrode, a pulse width programmed for each activated electrode, and a frequency programmed for each activated electrode.

The method 500 includes a step 525, in which the treatment protocol is sent to the implanted medical device along with the associated data file for storage.

The method 500 includes a step 530, in which the treatment protocol is sent to a remote electronic database along with the associated data file for storage.

It is understood that additional process steps may be performed before, during, or after the steps 505-540. For example, the method 500 may include a step of generating a plurality of data files over time (i.e., a history of the pain/stimulation maps), wherein each data file corresponds to a data-reduced sensation map at a different point in time, and sending the plurality of data files to the implanted medical device for storage. For reasons of simplicity, other additional processes are not specifically discussed herein. Furthermore, the steps 505-530 need not be performed in the numerical order shown in FIG. 16. For example, the step 530 may be performed before the step 525.

Figure 17:
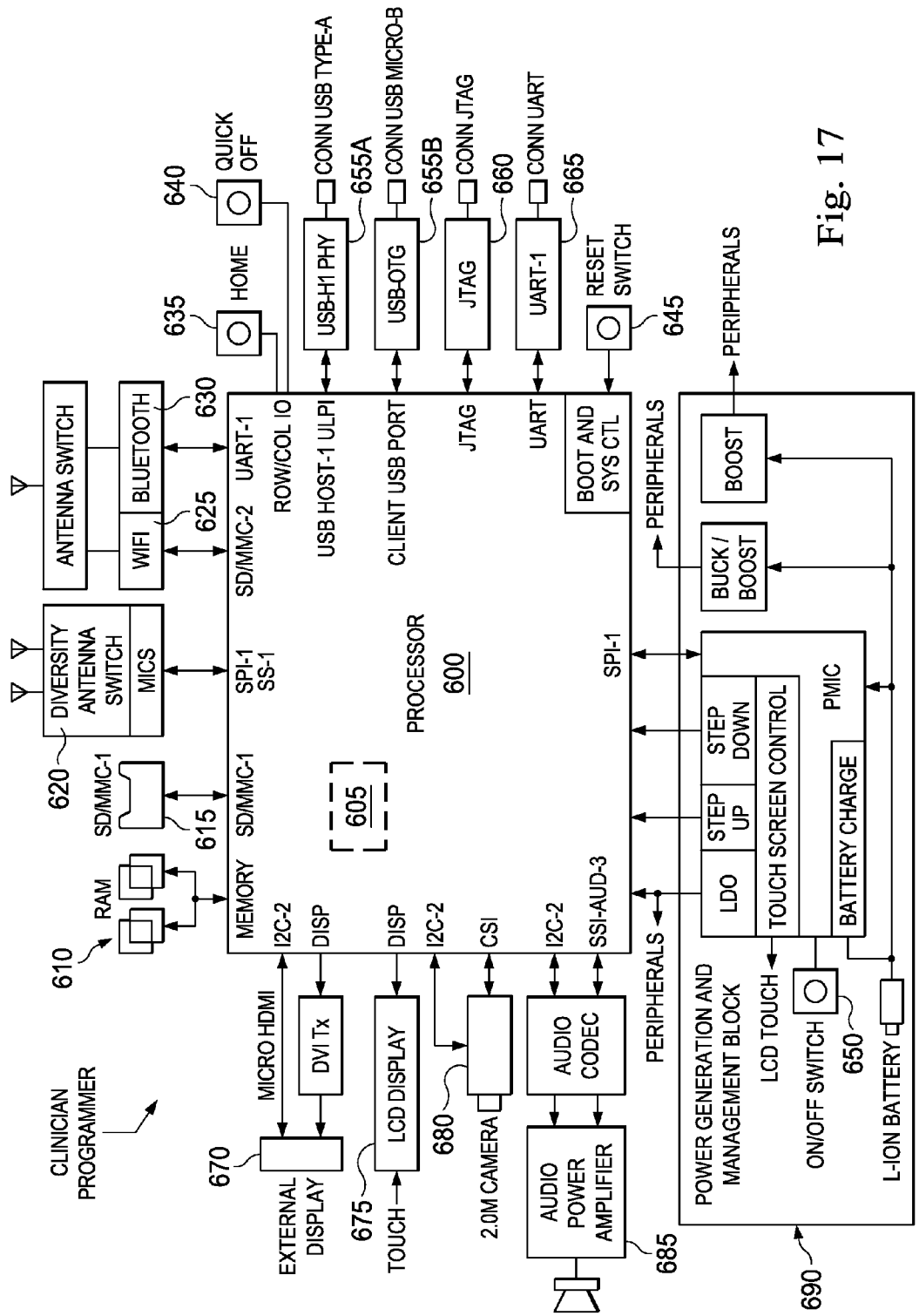
FIG. 17 is a simplified block diagram of an electronic programmer according to various aspects of the present disclosure.

FIG. 17 shows a block diagram of one embodiment of the electronic programmer (CP) discussed herein. For example, the electronic programmer may be a clinician programmer (CP) configured to generate, display, compress, and send the sensation maps discussed above. It is understood, however, that alternative embodiments of the electronic programmer may be used to perform these representations as well.

The CP includes a printed circuit board ("PCB") that is populated with a plurality of electrical and electronic components that provide power, operational control, and protection to the CP. With reference to FIG. 17, the CP includes a processor 600. The processor 600 controls the CP. In one construction, the processor 600 is an applications processor model i.MX515 available from Free scale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX51CEC, Rev. 4" data sheet dated August 2010 and published by Free scale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 17 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 17.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The Wi-Fi portion 625 and Bluetooth portion 630 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 17.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 17) may also be included for data transfer.

It is understood that a patient programmer may be implemented in a similar manner as the clinician programmer shown in FIG. 17.

Figure 18:
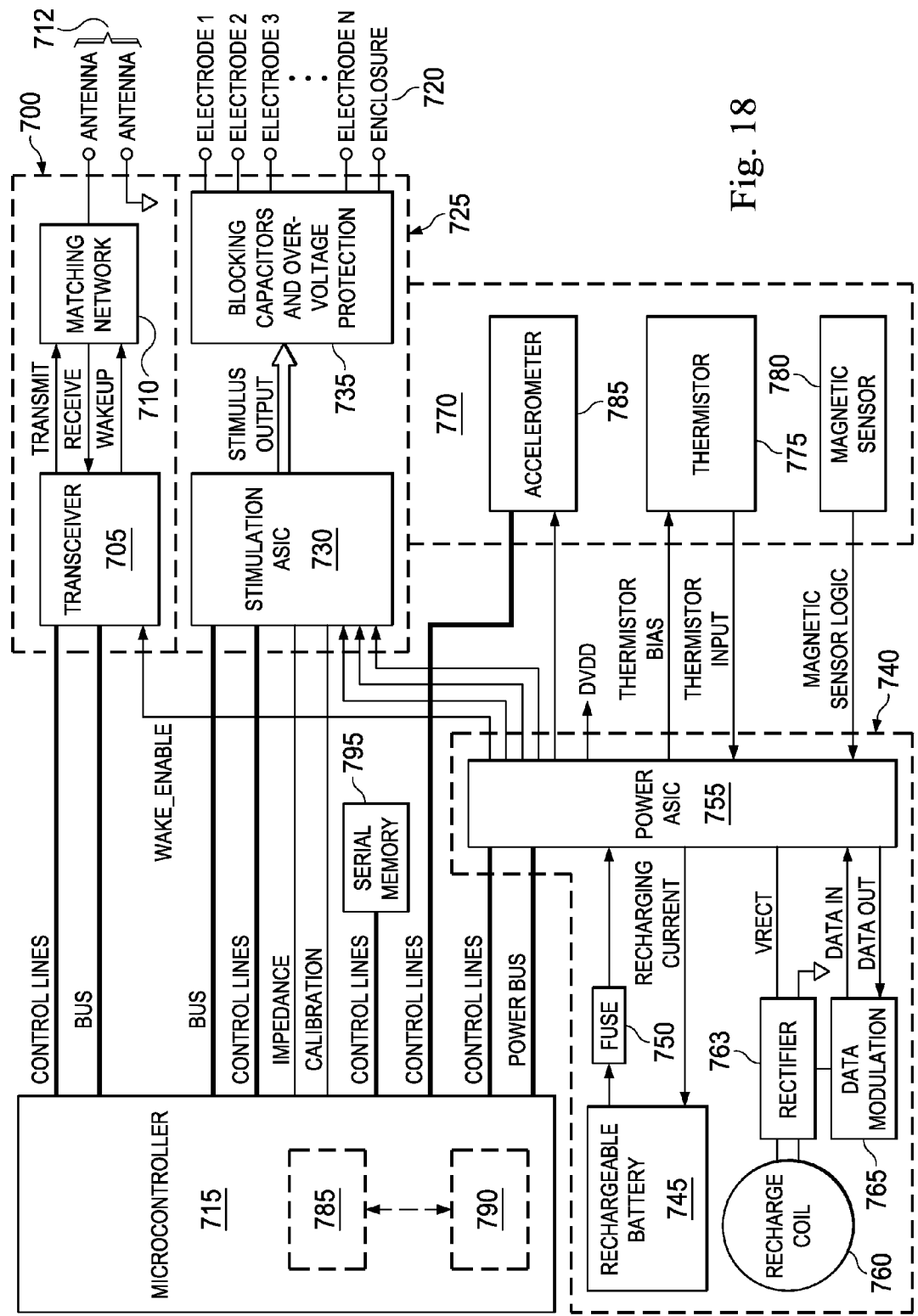
FIG. 18 is a simplified block diagram of an implantable medical device according to various aspects of the present disclosure.

FIG. 18 shows a block diagram of one embodiment of an implantable medical device. In the embodiment shown in FIG. 18, the implantable medical device includes an implantable pulse generator (IPG). The IPG includes a printed circuit board ("PCB") that is populated with a plurality of electrical and electronic components that provide power, operational control, and protection to the IPG. With reference to FIG. 18, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 18, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 18 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 19:
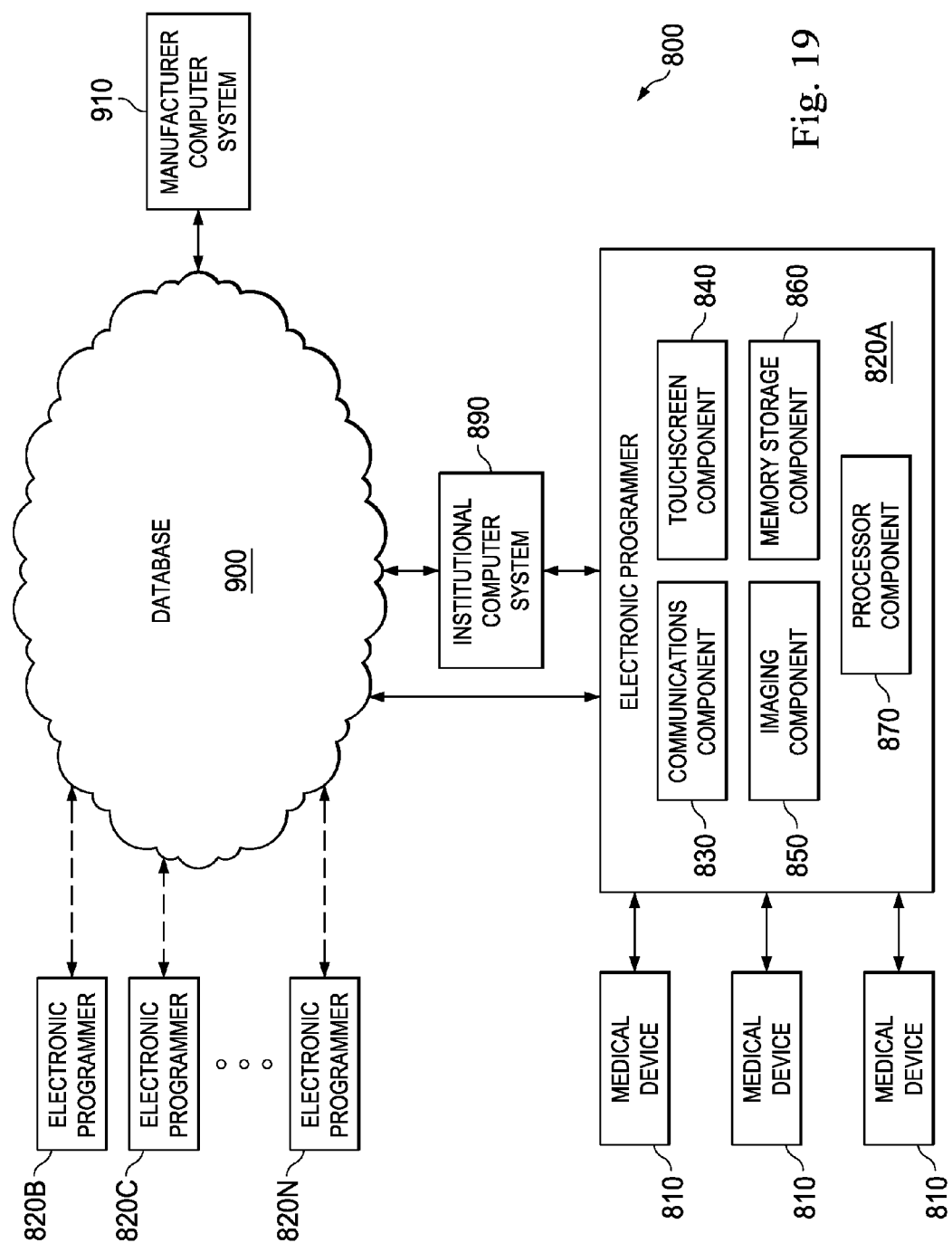
FIG. 19 is a simplified block diagram of a medical system/infrastructure according to various aspects of the present disclosure.

Referring now to FIG. 19, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 18), an implantable lead, a charger, or portions thereof. It is understood that each of the medical devices 810 may be a different type of medical device. In other words, the medical devices 810 need not be the same type of medical device. The medical device 810 includes a memory storage component configured to store data. In some embodiments, the memory storage component is partitioned into multiple partitions that are each configured to store a different type of data.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 17. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 19 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, the sensation maps may be uploaded from the electronic programmer 820A to the database 900. The sensation maps saved in the database 900 may thereafter be downloaded by any of the other electronic programmers 820B-820N communicatively coupled to it, assuming the user of these programmers has the right login permissions. For example, a compressed sensation map is generated by the electronic programmer 820A and uploaded to the database 900. That compressed map can then be downloaded by the electronic programmer 820B, which can use the downloaded compressed sensation map to reconstruct or recreate the original uncompressed sensation map. In this manner, a less data-intensive sensation map may be derived from a data-heavy sensation map, sent to a different programmer through the database, and then be used to reconstruct the original sensation map.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

According to the various aspects of the disclosure, the electronic programmer 820 can generate and then compress a data-heavy pain/stimulation map and produce a data file that can be used to reconstruct the pain/stimulation map. The data file may then be sent to the medical device 810 for storage. The data file may also be sent to the database 900 for storage. The data file may later be retrieved (from the medical device 810 or from the database 900) by the same electronic programmer 820 or another electronic programmer to reconstruct the original pain/stimulation map.

Figure 20A:
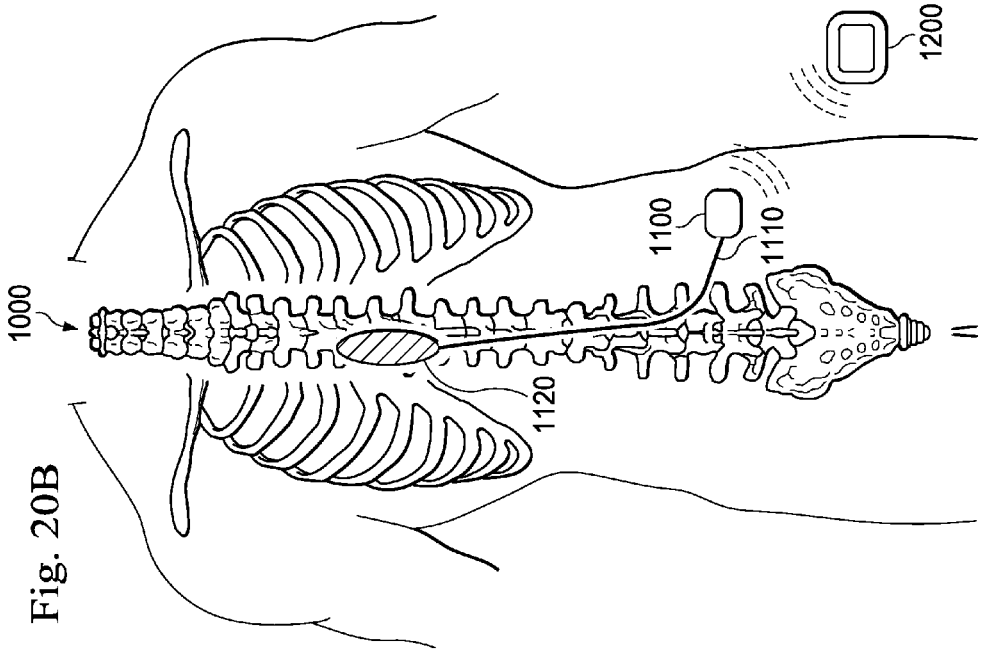
FIGS. 20A and 20B are side and posterior views of a human spine, respectively.
Figure 20B:
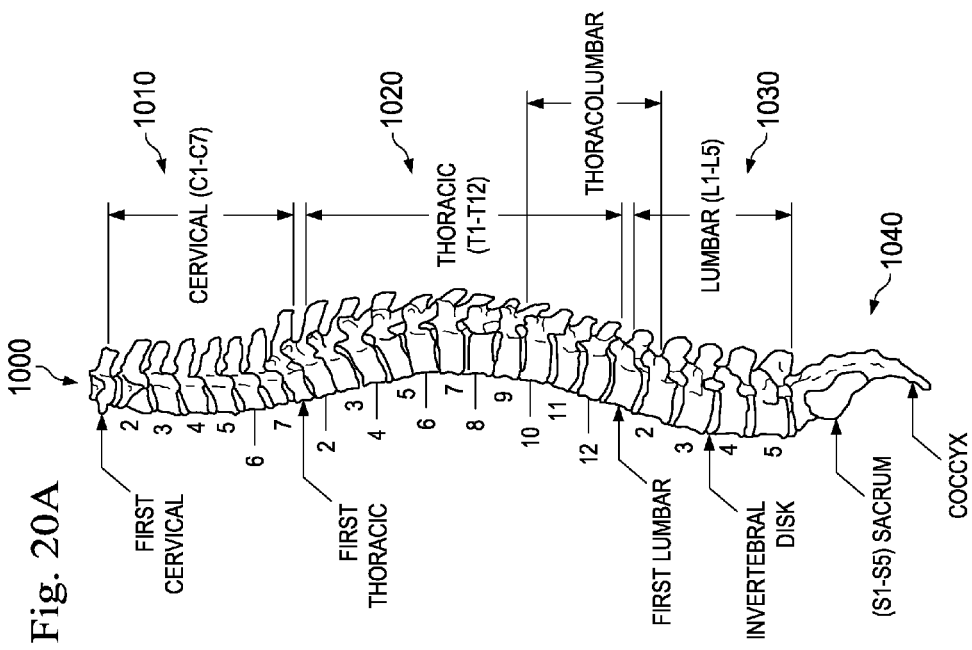

FIG. 20A is a side view of a spine 1000, and FIG. 20B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 20B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 17.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An electronic device for data-reducing and transmitting a sensation map of a patient, the electronic device comprising:
   a memory storage component configured to store programming code; and a computer processor configured to execute the programming code to perform the following tasks:
providing a sensation map associated with the patient wherein the sensation map comprises a pain map that includes a graphical depiction of pain experienced by the patient or a stimulation map that includes a graphical depiction of paresthesia experienced by the patient in response to electrical stimulation, and wherein the providing the sensation map comprises generating the sensation map over a three-dimensional (3D) human body model;
generating a data file having a data size less than a data size of the sensation map, wherein the data file contains digital information allowing a reconstruction of the sensation map;
establishing electronic communication with an implanted medical device located inside the patient's body; and
thereafter sending the data file to the implanted medical device for storage.

2. The electronic device of claim 1, wherein the generating the data file comprises:
performing a Connected Component Labeling (CCL) process to the sensation map to generate a processed image of the sensation map;
generating a plurality of data files by executing a plurality of data compression algorithms to the processed image of the sensation map, respectively, the data compression algorithms being selected from the group consisting of: Chain Code, Minimum Perimeter Polygon, Estimation with Primitives, Fourier descriptors, and run-length encoding;
computing a respective data size for each of the data files; and
selecting the data file with a smallest data size as the data file to be sent to the implanted medical device.

3. The electronic device of claim 1, wherein the tasks further comprise:
associating a treatment protocol with the sensation map, the treatment protocol including one or more of the following information: a date of sensation map creation, a type of implant lead containing electrodes configured to deliver electrical stimulation to the patient, an activated electrode configuration on the implant lead, a polarity programmed for each activated electrode, an amount of current programmed for each activated electrode, a pulse width programmed for each activated electrode, and a frequency programmed for each activated electrode; and
sending the treatment protocol to the implanted medical device along with the associated data file for storage.

4. The electronic device of claim 3, wherein the tasks further comprise:
generating a plurality of data files over time, wherein each data file corresponds to a data-reduced sensation map at a different point in time; and
sending the plurality of data files to the implanted medical device for storage.

5. The electronic device of claim 1, wherein the 3D human body model is customized to the patient based on physical characteristics of the patient that include one or more of the following: height, weight, age, gender, and ethnicity.

6. The electronic device of claim 1, further comprising: uploading the data file to a remote electronic database.

7. The electronic device of claim 1, wherein:
the electronic device is a portable clinician programmer having a touch-sensitive graphical user interface through which the sensation map is displayed; and
the implanted medical device includes a pulse generator configured to deliver electrical stimulation to the patient.

8. The electronic device of claim 1, wherein the generating of the sensation map comprises graphically depicting varying degrees of intensities of pain or stimulation.

9. The electronic device of claim 1, wherein the generating of the sensation map comprises graphically depicting different types of pain or different types of stimulation.

10. A medical system, comprising:
a neurostimulator configured to deliver electrical stimulation to a patient via one or more of a plurality of contacts located on a lead; and
a portable electronic programmer having an electronic processor and a touch-sensitive graphical user interface, wherein the electronic programmer is configured to:
provide a sensation map associated with the patient wherein the sensation map comprises a pain map that includes a graphical depiction of pain experienced by the patient or a stimulation map that includes a graphical depiction of paresthesia experienced by the patient in response to electrical stimulation, and wherein the electronic programmer is configured to provide the sensation map by generating the sensation map over a three-dimensional (3D) human body model;
generate a data file having a data size less than a data size of the sensation map, wherein the data file contains digital information allowing a reconstruction of the sensation map;
establish electronic communication with the neurostimulator; and
thereafter send the data file to the neurostimulator for storage.

11. The medical system of claim 10, wherein the electronic program is configured to generate the data file by:
performing a Connected Component Labeling (CCL) process to the sensation map to generate a processed image of the sensation map;
generating a plurality of data files by executing a plurality of data compression algorithms to the processed image of the sensation map, respectively, the data compression algorithms being selected from the group consisting of: Chain Code, Minimum Perimeter Polygon, Estimation with Primitives, Fourier descriptors, and run-length encoding;
computing a respective data size for each of the data files; and
selecting the data file with a smallest data size as the data file to be sent to the neurostimulator.

12. The medical system of claim 10, wherein the electronic programmer is further configured to:
associate a treatment protocol with the sensation map, the treatment protocol including one or more of the following information: a date of sensation map creation, a lead type, an activated electrode configuration on the lead, a polarity programmed for each activated electrode, an amount of current programmed for each activated electrode, a pulse width programmed for each activated electrode, and a frequency programmed for each activated electrode; and
send the treatment protocol to the neurostimulator along with the associated data file for storage.

13. The medical system of claim 12, wherein the electronic programmer is further configured to:

generate a plurality of data files over time, wherein each data file corresponds to a data-reduced sensation map at a different point in time; and send the plurality of data files to the neurostimulator for storage.

14. The medical system of claim 10, wherein the 3D human body model is customized to the patient based on physical characteristics of the patient that include one or more of the following: height, weight, age, gender, and ethnicity.

15. The medical system of claim 10, further comprising: a remote electronic database configured to store the data file.

16. The medical system of claim 10, wherein:
the electronic programmer is a clinician programmer having a touch-sensitive graphical user interface through which the sensation map is displayed.

17. The medical system of claim 10, wherein the generating of the sensation map comprises one of:
graphically depicting varying degrees of intensities of pain or stimulation; and
graphically depicting different types of pain or different types of stimulation.

18. A method of storing a sensation map, the method comprising:
providing a sensation map associated with a patient, wherein the sensation map comprises a pain map that includes a graphical depiction of pain experienced by the patient or a stimulation map that includes a graphical depiction of paresthesia experienced by the patient in response to electrical stimulation, and wherein the providing the sensation map comprises generating the sensation map over a three-dimensional (3D) human body model;
generating a data file having a data size less than a data size of the sensation map, wherein the data file contains digital information allowing a reconstruction of the sensation map;
establishing electronic communication with an implanted medical device located inside the patient's body; and
thereafter sending the data file to the implanted medical device for storage.

19. The method of claim 18, wherein generating the data file comprises:
performing a Connected Component Labeling (CCL) process to the sensation map to generate a processed image of the sensation map;
generating a plurality of data files by executing a plurality of data compression algorithms to the processed image of the sensation map, respectively, the data compression algorithms being selected from the group consisting of: Chain Code, Minimum Perimeter Polygon, Estimation with Primitives, Fourier descriptors, and run-length encoding;
computing a respective data size for each of the data files; and
selecting the data file with a smallest data size as the data file to be sent to the implanted medical device.

20. The method of claim 18, further comprising:
associating a treatment protocol with the sensation map, the treatment protocol including one or more of the following information: a date of sensation map creation, a type of implant lead containing electrodes configured to deliver electrical stimulation to the patient, an activated electrode configuration on the implant lead, a polarity programmed for each activated electrode, an amount of current programmed for each activated electrode, a pulse width programmed for each activated electrode, and a frequency programmed for each activated electrode; and
sending the treatment protocol to the implanted medical device along with the associated data file for storage.

21. The method of claim 20, further comprising:
generating a plurality of data files over time, wherein each data file corresponds to a data-reduced sensation map at a different point in time; and
sending the plurality of data files to the implanted medical device for storage.

22. The method of claim 18, wherein the 3D human body model is customized to the patient based on physical characteristics of the patient that include one or more of the following: height, weight, age, gender, and ethnicity.

23. The method of claim 18, further comprising: uploading the data file to a remote electronic database.

24. The method of claim 18, wherein:
the providing, the generating, the establishing, and the sending are performed by a clinician programmer having a touch-sensitive graphical user interface through which the sensation map is displayed; and
the implanted medical device includes a pulse generator configured to deliver electrical stimulation to the patient.

25. The method of claim 18, wherein the generating of the sensation map comprises graphically depicting varying degrees of intensities of pain or stimulation.

26. The method of claim 18, wherein the generating of the sensation map comprises graphically depicting different types of pain or different types of stimulation.

27. A programmable pulse generator for delivering a stimulation therapy to a patient, comprising:
a transceiver configured to electronic data via electronic communication conducted with an external clinician programmer;
a memory storage configured to store the electronic data, wherein the electronic data includes:
a stimulation program containing programming instructions for operating the programmable pulse generator; and
a data file having a smaller data size than a sensation map and containing digital information allowing reconstruction of the sensation map that graphically depicts, on the external clinician programmer, a sensation experienced by the patient stimulation program, wherein the sensation map comprises is generated over a three-dimensional (3D) human body model, and wherein the sensation map comprises a pain map that includes a graphical depiction of pain experienced by the patient or a stimulation map that includes a graphical depiction of paresthesia experienced by the patient in response to the stimulation therapy; and
a microcontroller and stimulation circuitry configured to generate electrical pulses of the stimulation therapy based on the stimulation program.

28. The programmable pulse generator of claim 27, wherein the data file is a compressed version of the sensation map.

29. The programmable pulse generator of claim 27, wherein the electronic data further includes a treatment protocol associated with the sensation map, the treatment protocol containing one or more of the following: a date of sensation map creation, a type of implant lead containing electrodes configured to deliver electrical stimulation to the patient, an activated electrode configuration on the implant lead, a polarity programmed for each activated electrode, an amount of current programmed for each activated electrode, a pulse width programmed for each activated electrode, and a frequency programmed for each activated electrode.

30. The programmable pulse generator of claim 29, wherein the electronic data further includes a plurality of data files that each correspond to data-reduced sensation map at a different point in time.

31. The programmable pulse generator of claim 27, wherein the generating of the sensation map comprises graphically depicting varying degrees of intensities of pain or stimulation.

32. The programmable pulse generator of claim 27, wherein the generating of the sensation map comprises graphically depicting different types of pain or different types of stimulation.

33. The programmable pulse generator of claim 27, wherein the 3D human body model is customized to the patient based on physical characteristics of the patient that include one or more of the following: height, weight, age, gender, and ethnicity.

* * * * *